United States Patent [19]

Roll

[11] Patent Number: 5,705,332
[45] Date of Patent: Jan. 6, 1998

[54] DETECTION AND IDENTIFICATION OF SALMONELLA AND SHIGELLA

[75] Inventor: Bruce Roll, Honolulu, Hi.

[73] Assignee: University of Hawaii, Honolulu, Hi.

[21] Appl. No.: 232,778

[22] Filed: Apr. 25, 1994

[51] Int. Cl.⁶ .............................. C12Q 1/68; C12P 19/34
[52] U.S. Cl. .................................... 435/6; 435/91.2
[58] Field of Search .......................... 435/6, 91.2, 973; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Anton et al. | 435/94 |
| 5,139,940 | 8/1992 | Isaacs et al. | 435/91 |
| 5,221,608 | 6/1993 | Cimino et al. | 435/6 |

FOREIGN PATENT DOCUMENTS

| | | | |
|---|---|---|---|
| 0409159A2 | 1/1991 | European Pat. Off. | C12Q 1/68 |
| WO/92/01056 | 1/1992 | WIPO | C12N 14/31 |
| WO/9304202 | 3/1993 | WIPO | C12Q 1/68 |

OTHER PUBLICATIONS

M. Ho et al., "Rotavirus as a cause of diarrheal morbidity and mortality in the United States," J. Infect. Dis., 158:1112–1116, (1988).

J.D. Snyder and M.H. Merson, "The magnitude of the global problem of acute diarrheal disease: a review of active surveillance data," Bull. World Health Organ., 60:605–613 (1982).

T.L. Hale, "Genetic basis of virulence in Shigella species," Microbiol. Rev., 55:206–224 (1991).

Singh and McFeters, "Detection methods for waterborne pathogens," pp. 125–156, in R. Mitchell (ed.), Environmental Microbiology, Wiley–Liss, New York, (1992).

Makintubee et al., "Shigellosis outbreak associated with swimming," Am. J. Public Health 77:166–168 (1987).

F.J. Sorvillo et al., "Shigellosis associated with recreational water contact in Los Angeles County," Am. J. Trop. Med. Hyg., 38:613–617 (1988).

T.C. Hazen and G.A. Toranzos, "Tropical Source Water," p. 33, in G.A. McFeters, Drinking Water Microbiology, Springer–Verlag, New York (1990).

J.J. Byrd et al., "Viable but nonculturable bacteria in drinking water," Appl. Environ. Microbiol., 57:875–878 (1991).

C. Desmonts et al, "Fluorescent–antibody method useful for detecting viable but nonculturable Salmonella spp. in chlorinated wastewater," Appl. Environ. Microbiol., 56:1448–1442 (1990).

J.J. Byrd and R.R. Colwell, "Maintenance of plasmids pBR322 and pUC8 in nonculturable Escherichia coli in the marine environment," Appl. Environ. Microbiol., 56:2104–2107 (1990).

A.P. Dufour, "E. coli: the fecal coliform", in A.W. Hoadley and B.J. Dutka, Bacterial Indicators/Health Hazards Associated with Water, ASTM, Philadelphia, p. 48, (1976).

V.J. Cabelli, Health Effects Criteria for Marine Recreational Waters, EPA–600/1–80–031, pp. 11–12 (Aug., 1983).

R.W. Kehr and C.T. Butterfield, "Notes on the relationship between coliforms and enteric pathogens," Public Health Repts. 58:589–596 (1943).

Batik et al., "Routine monitoring and waterborne disease outbreaks," J. Environ. Health 45:227–230 (1984).

American Public Health Association–American Water Works Association–Water Pollution Control Federation, Standard Methods for the Examination of Water and Wastewater, 16th ed., APHA, Washington, D.C., (1985).

D.J. Reasoner and E.E. Geldreich, "Rapid detection of water–borne fecal coliforms by $^{14}CO_2$ release," in A.N. Sharpe and D.S. Clark (eds.) Mechanizing Microbiology, Charles C. Thomas Publishers, pp. 120–139 (1978).

E.W. Frampton and L. Restaino, "Methods for Escherichia coli identification in food, water and clinical samples based on beta–glucuronidase detection," J. Appl. Bacteriol., 74:223–233 (1993).

G.W. Chang et al., "Proportion of β–D–glucuronidse–negative Escherichia coli in human fecal samples," Appl. Environ. Microbiol., 55–335–339 (1989).

R.S. Wensel et al., "Evaluation of coliphage detection as a rapid indicator of water quality," Appl. Environ. Microbiol., 43:430–434 (1982).

Y. Kott et al., "Bacteriophages as bacterial viral pollution indicators," Water Res., 8:165–171 (1982).

A.H. Havelaar et al., "Factors effecting the enumeration of coliphages in sewage and sewage–polluted waters," Antonie van Leeuwenhoek 49:387–397 (1983).

B.J. Dutka, "Coliforms are inadequate index of water quality," J. Environ. Health 36:39–46 (1973).

P. Zwadyk, "Enterobacteriaceae: Salmonella and Shigella intestinal pathogens," pp. 613–622 in W.K. Joklik et al., (eds), Zinsser Microbiology, 18th edition, Appleton Century Crofts, Norwalk, CT, (1984).

R.J. Steffan and R.M. Atlas, "Polymerase chain reaction: Applications in environmental microbiology," Ann. Rev. Microbiol., 45:137–161 (1991).

Tsen et al., "DNA sequence of a Salmonella–specific DNA fragment and the use of oligonucleotide probes for Salmonella detection," Appl. Microbiol. Biotechnol., 35:339–347 (1991).

Tsen et al., "Possible use of a 1.8 kb DNA fragment for the specific detection of Salmonella in foods," J. Ferment. Bioeng. 68:1–6 (1989).

D.L. Kacian et al., Proc. Nat. Acad. Sci USA 69:3038 (1972).

(List continued on next page.)

Primary Examiner—Eggerton A. Campbell
Attorney, Agent, or Firm—Medlen & Carroll, LLP

[57] ABSTRACT

The present invention is directed to methods and reagents for the specific detection and presumptive identification of various bacteria associated with waterborne infectious disease. In particular, this invention relates to methods and reagents for the specific detection and identification of Salmonella and Shigella in environmental samples such as water and sewage.

14 Claims, 13 Drawing Sheets

OTHER PUBLICATIONS

M. Chamberlin et al., Nature 228:227 (1970).

D.Y. Wu and R.B. Wallace, Genomics 4:560 (1989).

*PCR Technology*, H.A. Erlich (ed.) (Stockton Press 1989).

K.B. Mullis, et al., Cold Spring Harbor Symposia, vol. II, pp. 263–273 (1986).

Anderson and Young, Quantitative Filter Hybridisation, in *Nucleic Acid Hybridisation* (1985).

A.K. Bej et al., "Polymerase chain reaction–gene probe detection of microorganisms by using filter–concentrated samples," Appl. Environ. Microbiol., 57:3529–3534 (1991).

Y.-L Tsai and B.H. Olson, "Rapid methods for separation of bacterial DNA from humic substances for polymerase chain reaction," Appl. Environ. Microbiol., 58:2292–2295 (1991).

Y.-L Tsai et al., "Detection of *Escherichia coli* in sewage and sludge by polymerase chain reaction," Appl. Environ. Microbiol., 59:353–357 (1993).

E.M. Southern, "Detection of specific sequences among DNA fragments separated by gel electrophoresis," J. Mol. Biol., 98:503–517 (1975).

Sambrook et al., *Molecular Cloning: A Laboratory Manual*, 2d ed., Cold Spring Harbor Laboratory, Cold Spring Harbor, NY (1989).

Hartman et al., "Sequence and molecular characterization of a multicopy invasion plasmid antigen gene, ipaH, of *Shigella flexneri*," J. Bacteriol., 172:1905–1915 (1990).

The Genius System User's Guide for Filter Hybridization, Version 2.0, Boehringer Mannheim Biochemicals, Indianapolis, IN, Cat. No. 101023, 84 pp. (1992).

Shyamala and Ames, "Amplification of bacterial genomic DNA by the polymerase chain reaction and direct sequencing after asymmetric amplification: application to the study of periplasmic permeases," J. Bacteriol., 171:1602–1608 (1989).

Bej et al., "Detection of coliform bacteria in water by polymerase chain reaction and gene probes," Appl. Environ. Microbiol., 56:307–314 (1990).

Bej et al., "Multiplex PCR amplification and immobilized capture probes for detection of bacterial pathogens and indicators in water," Mol. Cell. Probes 4:353–365 (1990).

Widjojoatmodjo et al., "Evaluation of the magnetic immuno PCR assay for rapid detection of Salmonella," Eur. J. Clin. Microbiol. Infect. Dis., 10:935–938 (1991).

Widjojoatmodjo et al., "The magnetic immuno polymerase chain reaction assay for direct detection of Salmonellae in fecal samples," J. Clin. Microbiol., 30:3195–3199 (1992).

Rahn et al., "Amplification of an invA gene sequence of *Salmonella typhimurium* by polymerase chain reaction as a specific method of detection of Salmonella," Mol. Cell. Probes 6:271–279 (1992).

Atlas et al., "Detection of indicator bacteria and pathogens in water by polymerase chain reaction (PCR) and gene probe methods," in Biotechnology and Environmental Science: Molecular Approaches, edited by S. Mongkolsuk et al. (Plenum Press, New York, 1992).

Toranzos and Alvarez, "Solid–phase polymerase chain reaction: applications for direct detection of enteric pathogens in waters," Can. J. Microbiol., 38:365–369 (1992).

Aabo et al., "Salmonella identification by the polymerse chain reaction," Mol. Cell. Probes 7:171–178 (1993).

Luk et al., "Selective amplification of abequose and paratose synthase genes (rib) by polymerase chain reaction for identification of Salmonella major serogroups (A, B,C2, and D)," J. Clin. Microbiol., 31:2118–2123 (1993).

Cohen et al., "Genus–specific detection of Salmonellae using the polymerase chain reaction (PCR)," J.Vet. Diag. Invest., 5:368–371 (1993).

Doran et al., "DNA–based diagnostic tests for Salmonella species targeting agfA, the structural gene for thin, aggregative fimbriae," J. Clin. Microbiol., 31:2263–2273 (1993).

Way et al., "Specific detection of Salmonella spp. by multiplex polymerase chain reaction," Appl. Environ. Microbiol., 59:1473–1479 (1993).

Song et al., "Detection of *Salmonella typhi* in the blood of patients with typhoid fever by polymerase chain reaction," J. Clin. Microbiol., 31:1439–1443 (1993).

Josephson et al., "Polymerase chain reaction detection of nonviable bacterial pathogens," Appl. Environ. Microbiol., 59:3513–3515 (1993).

Fluit et al., "Rapid detection of Salmonellae in poultry with the magnetic immuno–polymerase chain reaction," Appl. Environ. Microbiol., 59:1342–1346 (1993).

F.W. Hickman et al., "*Salmonella typhi*: Identification, Antibiograms, Serology and Bacteriophage Typing," Am. J. Med. Technol., 44 o 2 o 78:1149–1159 (1978).

A.K. Bej et al., "Applications of the Polymerase Chain Reaction in Environmental Microbiology," PCR Methods Appl., 1:151–159 (1992).

R. Meyer et al., "Direct detection by polymerase chain reaction (PCR) of *Escherichia coli* in water and soft cheese and identification of enterotoxigenic strains," Appl. Microbiol., 13:268–271 (1991).

O. Olsvik et al., "Magnetic Separation Techniques in Diagnostic Microbiology," Clin. Microbiol. Rev. 7:43–54 (1994).

G. Spierings et al., "Characterization of the *Salmonella typhimurium* phoE gene and development of Salmonella–specific DNA probes," Gene 122:45–52 (1992).

V. Shyamala et al., "Genome walking by single–specific–primer polymerase chain reaction: SSP-PCR," Gene 84:1–8 (1989).

B. Oyofo et al "Specific Detection of *Campylobacter jejuni* and *Campylobacter coli* by Using Polymerase Chain Reaction," J. Clin. Microbiol., 30:2613–2619 (1992).

M.S. Islam et al., "Use of the Polymerase Chain Reaction and Fluorescent–Antibody Methods for Detecting Viable but Nonculturable *Shigella dysenteriae* Type 1 in Laboratory Microcosms," Appl. Envir. Microbiol., 59:536–540 (1993).

B.H. Olson et al., "Molecular Approaches to Environmental Management," pp. 239–263, in R. Mitchell (ed.), Environmental Microbiology, (Wiley–Liss, New York, 1992).

M.W. Rhodes et al., "Survival of *Escherichia coli* and Salmonella sp. in Estuarine Environments," Appl. Envir. Microbiol., 54:2902–2907 (1988).

R.S. Flowers et al., "Visual Immunoassay for Detection of Salmonella in Foods: Collaborative Study," J. Assoc. Off. Anal. Chem., 71:975–980 (1988).

L.W. Slanetz, "Coliforms, Fecal Streptococci and Salmonella in Seawater and Shellfish," H.L.S. 5:66–78(1968).

V.J. Cabelli et al., "Relationship of Microbial Indicators to Health Effects as Marine Bathing Beaches," Am. J. Publ. Health 69:690–696 (1979).

P. Kabler, "Water Examinations by Membrane Filter and Most Probable Number Procedures," Am. J. Publ. Health, pp. 379–386 (1954).

R. Helmuth, "Molekularbiologische Grundlagen der Virulenz von Salmonellen und daraus resultierende neuere Nachweisverfahren," Dtsch. tierarztl. Wschr. 100:252–255 (1993).

FIG. 2

Isolation of Salmonella
from Environmental Water*

15 Tube MPN in Tetrathionate Broth
(Incubate 24 hours at 37°C)

↙ ↘

Streak Positive Tubes on
XLD
(Incubate 24 hours at 37°C)

↓

Pick Characteristic
Salmonella Colonies

Streak Positive Tubes on
Hektoen Enteric Agar
(Incubate 24 hours at 37°C)

↓

Pick Characteristic
Salmonella Colonies

↘ ↙

Inoculate Suspected Salmonella Colonies on TSI and LIA
(Incubate 24 hours at 37°C)

↓

Serotype Prospective Salmonella With Polyvalent "O" Antibody

↓

Calculate MPN/100 ml of Original Sample

*This procedure was conducted on both Membrex-concentrated samples and directly on sample water.

DETECTION AND IDENTIFICATION OF SALMONELLA AND SHIGELLA

FIELD OF THE INVENTION

The present invention relates to methods and reagents for the detection of enteric pathogens in environmental samples such as water, wastewater, sewage and sludge, as well as food, feed and clinical samples.

BACKGROUND OF THE INVENTION

An ever-enlarging world population has increased demands on water resources worldwide. Indeed, this population increase is directly proportional to the potential for surface and ground water contamination by pathogenic organisms associated with increased waste burdens. To ensure good public health, there is a need for readily available methods to detect and enumerate pathogens in water. Unfortunately, despite years of testing and research, no single procedure is available for the reliable detection of the major waterborne pathogens. Indeed, there are no standardized methods for detecting all of these pathogens. The methods that are available are usually time-consuming and expensive.

Routine or periodic monitoring of water for the presence of pathogens is essential in situations such as wastewater reclamation, during and after waterborne outbreaks, and for water sources with a frequent history of contamination. This is largely due to the observation that most enteric pathogens appear intermittently and in low concentrations in aquatic environments. Thus, potentially pathogenic organisms may be present in a water supply and go undetected, largely due to their low numbers and the limitations of current testing methods, including relatively low sensitivity levels.

Despite advances in public health technology, water and food remain important reservoirs of diarrheal and other diseases of humans and other animals. Infectious diarrhea represents a significant public health concern. According to one estimate, infectious diarrhea results in the hospitalization of 200,000 children in the United States each year, at an annual cost of one billion dollars (M. Ho et al., "Rotavirus as a cause of diarrheal morbidity and mortality in the United States," J. Infect. Dis., 158: 1112–1116, 1988).

Worldwide, waterborne disease is of even greater significance, with over 250 million reported cases of waterborne disease and more than 10 million deaths annually (J. D. Snyder and M. H. Merson, "The magnitude of the global problem of acute diarrheal disease: a review of active surveillance data," Bull. World Health Organ., 60: 605–613 [1982]). When other sources of diarrheal disease are taken into consideration the figures are even more staggering, with these diseases claiming the lives of over 5 million children per year in developing countries (T. L. Hale, "Genetic basis of virulence in Shigella species," Microbiol. Rev., 55: 206–224 [1991]).

Most of the cases of waterborne diarrheal disease result from the contamination of drinking water supplies with human fetal material. Contamination of ground water in local areas may occur through such mechanisms as seepage of sewage into aquifers and by improperly developed or poorly protected wells. When factors such as recreational exposure to contaminated salt and fresh water are also taken into consideration, diarrheal disease takes on even greater importance.

Various infectious agents are associated with human waterborne diseases, including Campylobacter, E. coli, Leptospira, Pasteurella, Salmonella, Shigella, Vibrio, Yersinia, Proteus, Giardia, Entoamoeba, Cryptosporidium, hepatitis A virus, Norwalk, parvovirus, polio virus, and rotavirus. Worldwide, the most common bacterial diarrheal diseases are associated with waterborne transmission of Shigella, Salmonella, pathogenic E. coli, Campylobacter jejuni, and Vibrio cholerae (Singh and McFeters, "Detection methods for waterborne pathogens," pp. 125–156, in R. Mitchell (ed.), Environmental Microbiology, [Wiley-Liss, New York, 1992]). Table 1 lists important characteristics of diseases associated with a few of the most significant organisms.

TABLE 1

Waterborne Diarrheal Bacterial Diseases Most Commonly Reported

| Organism | Disease | Incubation Period | Common Symptoms |
| --- | --- | --- | --- |
| Shigella sp. | Shigellosis | 1–7 days | Diarrhea, fever, cramps, tenesmus, dysentery* |
| Salmonella typhimurium | Salmonellosis | 6–72 hours | Abdominal pain, diarrhea, nausea, vomiting, fever |
| S. typhi | Typhoid fever | 1–3 days | Abdominal pain, fever, chills, diarrhea or constipation, intestinal hemorrhage |
| Pathogenic E. coli | Diarrhea | 12–72 hours | Diarrhea, fever, vomiting |
| Campylobacter jejuni | Gastroenteritis | 1–7 days | Abdominal pain suggesting acute appendicitis, fever, headache, malaise, diarrhea, vomiting |
| Proteus sp. | Scombroid fish poisoning | Few minutes to 1 hour | Headache, dizziness, vomiting, nausea, peppery taste, burning throat, facial swelling and flushing, stomach pain, itching |
| Yersinia enterocolitica | Yersiniosis | 24–36 hours | Severe abdominal pain, fever, headache |
| Vibrio parahaemolyticus | | 12 hours | Vomiting, diarrhea, abdominal pain, fever |
| Vibrio cholerae | Gastroenteritis | 1–3 days | Vomiting, diarrhea, dehydration |

Swimming-associated outbreaks caused by Shigella, Giardia, Norwalk-like viruses, and other enteroviruses have been well documented [See e.g., Makintubee et al., "Shigellosis outbreak associated with swimming," Am. J. Public Health 77: 166– 168 [1987]; F. J. Sorvillo et al., Shigellosis associated with recreational water contact in Los Angeles County," Am. J. Trop. Med. Hyg., 38: 613–617 [1988]).

The following table lists the majority of waterborne infectious bacteria which are associated with human diarrheal and non-diarrheal disease.

TABLE 2

Infectious Bacteria Transmitted by Water

| Organism | Commonly Associated Diseases in Humans |
| --- | --- |
| Acinetobacter calcoaceticus | Nosocomial infections |
| Aeromonas hydrophila | Enteritis, wound infections |
| A. sobria | |
| A. caviae | |

TABLE 2-continued

Infectious Bacteria Transmitted by Water

| Organism | Commonly Associated Diseases in Humans |
|---|---|
| *Campylobacter jejuni* | Enteritis |
| *C. coli* | |
| *Chromobacterium violaceum* | Enteritis |
| *Citrobacter* spp. | Nosocomial infections |
| *Clostridium perfringens*, type C | Enteritis |
| *Enterobacter* spp. | Nosocomial infections |
| *E. coli*, various serotypes | Enteritis |
| *Flavobacterium meninogsepticum* | Nosocomial infections, meningitis |
| *Francisella tularensis* | Tularemia |
| *Fusobacterium necrophorum* | Liver abscesses |
| *Klebsiella* spp. | Nosocomial infections, pneumonia |
| *Leptospira icterohaemorrahagia* and other *Leptospira* spp. | Leptospirosis |
| *Legionella pneumophila* and other *Legionella* spp. | Legionellosis |
| *Morganella morganii* | Urethritis, nosocomial infections |
| *Mycobacterium tuberculosis* | Tuberculosis |
| *M. marinum* and other *Mycobacterium* spp. | Granuloma, dermatitis |
| *Plesiomonas shigelloides* | Enteritis |
| *Pseudomonas pseudomallei* | Melioidosis |
| *Pseudomonas* spp. | Dermatitis, ear infections |
| *Salmonella enteritidis* | Enteritis (salmonellosis) |
| *S. montevideo* B | |
| *S. typhimurium* and other *Salmonella* serotypes | |
| *S. paratyphi* A and B | Paratyphoid fever |
| *S. typhi* | Typhoid fever |
| *Serratia marcesens* | Nosocomial infections |
| *Shigella* spp. | Dysentery |
| *Staphylococcus aureus* | Wounds, food poisoning |
| *Vibrio cholerae* | Cholera |
| *V. alginolyticus* | Enteritis |
| *V. fluvialis* | Wound infections |
| *V. mimicus* | |
| *V. parahaemolyticus* | |
| *V. vulnificus* | |
| Other *Vibrio* spp. | |
| *Yersinia enterocolitica* | Enteritis |

*After T. C. Hazen and G. A. Toranzos, "Tropical Source Water," p. 33, in G. A. McFeters, Drinking Water Microbiology [Springer-Verlag, New York, 1990]).

While the presence of pathogens in drinking and recreational waters presents a significant public health concern, recovery of pathogens from environmental samples is generally difficult. In addition to the usually low numbers of organisms present in the water, nutrient limitations and environmental stressors produce unpredictable physiological and morphological changes in these pathogens. This makes their isolation and identification problematic. Organisms injured due to these environmental stressors often exhibit atypical reactions and require specialized handling for their resuscitation (see e.g., Singh and McFeters, p. 132–133).

Often, organisms are present but are unculturable (Id., at 131–159; see also, J. J. Byrd et al., "Viable but nonculturable bacteria in drinking water," Appl. Environ. Microbiol., 57: 875–878 [1991]; C. Desmonts et al., "Fluorescent-antibody method useful for detecting viable but nonculturable Salmonella spp. in chlorinated wastewater," Appl. Environ. Microbiol., 56: 1448—1442 [1990]; and J. J. Byrd and R. R. Colwell, "Maintenance of plasmids pBR322 and pUC8 in nonculturable *Escherichia coli* in the marine environment," Appl. Environ. Microbiol., 56: 2104–2107 [1990]). Unless other methods are used for their detection (e.g., immunoassays) these viable, but non-culturable organisms may present an undetected threat to public health.

In addition, the methods commonly used to detect these pathogens were initially designed for clinical, rather than environmental samples. This is of significance in view of the different ecological niche occupied by clinical as compared with environmental isolates. Clinical isolates are usually provided needed nutrients by their host animal and are generally protected from harsh environmental conditions such as cold, heat, damaging chemicals and radiation. In contrast, environmental isolates must deal with these environmental conditions and effectively compete with organisms naturally present and adapted to life in the environment. Pathogenic organisms are rarely readily adaptable to prolonged survival in the environment. Thus, "indicator" organisms are used as a prognostic indication of whether pathogens may be present in a particular sample.

Use of Indicator Organisms to Detect Fecal Contamination of Water

Problems associated with recovery of pathogens from water led to the development of methods to detect and enumerate "indicators" of fecal contamination. These organisms serve to indicate whether a given water supply is contaminated with fecal material, without actually testing for the presence of pathogens. This contamination is viewed as predictive of the potential presence of enteric pathogens (i.e., without the presence of fecal material, the chances of these pathogens being present is usually remote). However, a number of issues remain to be resolved, not the least of which is the significance of the presence of indicator organisms in water supplies.

Criteria for the establishment of the "ideal" indicator include the following factors: 1) the indicator should always be present in the presence of pathogens; 2) the indicator should always be present in a predicable ratio with pathogenic organisms; 3) the indicator should be specific for fecal contamination; 4) the indicator should be able to resist water treatment and disinfection processes to the same or a slightly greater extent than the pathogens; and 5) the indicator should be detectable by simple and rapid methods.

Historically, "coliforms" have served as the indicator bacteria for fecal contamination in United States water supplies. However, term "coliform" encompasses four genera (Escherichia, Citrobacter, Enterobacter, and Klebsiella); many of these species are commonly found in the environment in the absence of fecal contamination. Although all of these genera may be recovered from domestic sewage in large numbers, only *E. coli* is consistently and exclusively found in feces (see e.g., A. P. Dufour, "*E. coli:* the fecal coliform, in A. W. Hoadley and B. J. Dutka, *Bacterial Indicators/Health Hazards Associated with Water,* [ASTM, Philadelphia, 1976], p. 48). Thus, coliform detections methods are not specific for the determination of whether a water supply has been contaminated with fecal matter. Nonetheless, regulations based on detection and enumeration of "total coliforms" have been in effect in the United States since 1914 (i.e., the Treasury Department Standards of 1914; subsequent standards have been promulgated by the U.S. Public Health Service, and presently, by the US. Environmental Protection Agency [EPA]).

Recognition of the fact that most of the organisms included in the designation "total coliforms" are not of fecal origin, led to the development of tests to detect "fetal coliforms," for a subgroup of thermotolerant organisms included within the total coliforms. However, this designation is also not specific, as it includes *E. coli,* as well as various Klebsiella strains. Despite the fact that although there are substantial extra-fecal sources of Klebsiella, and this organism is infrequently found in human feces, the use of the "fetal coliform" designation and tests to identify these organisms remain routine (reviewed by V. J. Cabelli, *Health Effects Criteria for Marine Recreational Waters*, EPA-600/1-80-031, [August, 1983], pp.11–12).

Furthermore, the correlation between coliform densities in water and the incidence of waterborne disease originally postulated by Kehr and Butterfield in 1943 (R. W. Kehr and C. T. Butterfield, "Notes on the relationship between coliforms and enteric pathogens," Public Health Repts. 58: 589–596 [1943]) have not been supported by experimental tests (Batik et at., "Routine monitoring and waterborne disease outbreaks," J. Environ. Health 45: 227–230 [1984]). Quite simply, there has been no direct evidence presented that the level of coliform contamination correlates well with waterborne disease outbreaks (see Pipes, p. 434–435). Nonetheless, due to the lack of better methods, the detection of coliforms as indicator bacteria continues into the present.

Coliform detection may be accomplished by various methods, including multiple tube fermentation (i.e., most probable number or "MPN" determinations), membrane filtration, the "presence-absence" test, and various rapid enzyme (e.g., the MUG test) and immunoassay methods. Important considerations with these methods include the large time, equipment and personnel commitment necessary to conduct and interpret these tests.

Coliform Detection Methods

Most Probable Number (MPN). The MPN method is a labor, time and supply intensive method, which involves three distinct stages of specimen processing (the presumptive (with lauryl tryptose broth), completed (with brilliant green lactose bile broth) and confirmed tests (with LES Endo or EMB). FIG. 1 illustrates the steps involved in MPN analysis for detection of coliforms. As is apparent from this figure, the MPN method requires 3–4 days in order to produce confirmatory results, and statistical analysis to quantitate the organisms present.

This procedure has been developed to separate organisms within the coliform group into "total" and "fecal" coliforms. Prior enrichment of organisms in a presumptive test medium is required for optimum recovery of fecal coliforms. These methods are used as confirmatory tests conducted with various selective media and elevated incubation temperatures (e.g., 44.5° C.). Thus, there is also a significant time and labor commitment associated with these methods.

Membrane Filtration. In membrane filtration, a known volume of water sample is passed through a membrane filter which is then placed on growth media (e.g., M-Endo or LES-Endo), and incubated overnight. All colonies with characteristics common to coliforms are considered to be members of the coliform group. An advantage of membrane filtration is that preliminary results are usually available in 24 hours. However, verification of colony identification is recommended, usually requiring additional days in order to conduct the needed biochemical tests.

Additional disadvantages with the membrane filtration method include fouling of membranes with debris and suspended solids present in water. These particulates prevent free flow of water through the membrane, greatly slowing the process. In addition, the presence of particulate material on the membrane often interferes with organism growth, preventing reliable identification of bacteria. In this situation, reliable enumeration estimates are also precluded due to the presence of visible particulates present on the membrane which may be confused with colonies, the possibility that colonies are present under the particulate matter, yet not be visible for counting, and the potential interference with organism growth due to the composition of the particulates (e.g., the particulate may be comprised of a material toxic to the organisms).

Membrane filtration methods are especially unsuitable for use with "dirty" water. This is a significant consideration in many settings, especially testing of environmental waters.

Membrane Filtration Method Modifications. A seven hour fecal coliform test similar to the membrane filtration process has also been described. In this technique, the water sample is filtered and the filter placed on M-7 FC agar and incubated at 41.5° C. [American Public Health Association-American Water Works Association-Water Pollution Control Federation, *Standard Methods for the Examination of Water and Wastewater*, 16th ed., [APHA, Washington, D.C.], 1985; hereinafter, "Standard Methods"}. Yellow colonies representing fecal coliforms are enumerated after seven hours of incubation. However, different growth rates of colonies necessitate a compromise between sensitivity of detection and enumeration. That is to say, because different organisms grow at different rates, some organisms will not have had sufficient time to produce visible colonies on the medium by the time enumeration is conducted.

The value of this test is perhaps questionable, in view of its deletion from the most recent edition of Standard Methods.

Another method developed by Reasoner, in conjunction with Geldrich [D. J. Reasoner and E. E. Geldreich, "Rapid detection of water-borne fetal coliforms by $^{14}CO_2$ release," in A. N. Sharpe and D. S. Clark, (eds.) *Mechanizing Microbiology*, [Charles C. Thomas Publishers, 1978], pp. 120–139) involves concentration of bacteria on a membrane filter which is then placed in M-FC broth which contains radiolabelled $^{14}C$-mannitol. Major problems with these methods involve the use of radioactivity and the attendant disposal and handling concerns, as well as the need for specialized and expensive instruments. The tubes are incubated for 2 hours at 35° C., followed by 2.5 hours at 44.5°. Release of $^{14}CO_2$ due to microbial metabolism is then assayed by liquid scintillation spectrometry.

An alternate radioactive test was developed by Dange et al. (V. Dange et al., "One hour portable test for drinking waters," Water Res., 22:133–137 [1988]). This method is based on the correlation of $^{32}P$ uptake by organisms present in a water sample incubated in a synthetic medium. Thus, these methods require highly trained laboratory personnel and are not suitable for use in many labs.

Presence-Absence Test. The presence-absence test to detect the presence of coliforms involves the inoculation of broth with 100 ml samples of water, followed by incubation at 25° C. for 24–48 hours. If acid and gas is produced in the medium, the test is positive for the presence of coliforms (see e.g., Standard Methods, at p. 882–884). No enumeration of organisms is attempted, nor are any identification methods utilized. Thus, the information garnered from this method is very limited.

Fluorometric and Enzymatic Tests. Detection methods for coliforms with fluorometric tests and numerous variations on the basic technology have also been developed. Other substrate-based methods include the use of such compounds as ortho-nitrophenyl-β-D-galactopyranoside (ONPG) and 4-methylumbelliferyl-β-D-glucuronide (MUG). These methods utilize fluorogenic or chromogenic substrates to detect coliform metabolism, as opposed to direct detection and enumeration of organisms. Thus, the only data available from these test methods relate to the presence or absence of organisms which possess the necessary enzymatic machinery to produce the detectable color compounds from a given substrate.

The MUG test is also problematic in that many clinically important *E. coli* strains are negative. For example, the highly virulent and very difficult to treat, *E. coli* 0157:H7 serotype associated with recent foodborne disease outbreaks is negative in this test (see e.g., E. W. Frampton and L. Restaino, "Methods for *Escherichia coli* identification in food, water and clinical samples based on beta-glucuronidase detection," J. Appl. Bacteriol., 74: 223-233 [1993]). Indeed, there is a large proportion of β-glucuronidase negative *E. coli* (see e.g., G. W. Chang et al., "Proportion of β-D-glucuronidase-negative *Escherichia coli* in human fecal samples," Appl. Environ. Microbiol., 55: 335-339 [1989]). Furthermore, species within other genera such as Staphylococcus, Streptococcus, Clostridium, and the anaerobic corynebacteria also produce β-glucuronidase (Frampton and Restaino, p. 223). Thus, not only is the test not highly sensitive, it is not specific. These reports raise serious questions regarding the reliability of these testing methods.

Bacteriophages. In addition to culture and enzymatic detection methods, bacteriophages have also been used with some limited success as indicators of fecal contamination (R. S. Wensel et al., "Evaluation of coliphage detection as a rapid indicator of water quality," Appl. Environ. Microbiol., 43: 430-434 [1982]; Y. Kott et al., "Bacteriophages as bacterial viral pollution indicators," Water Res., 8: 165-171 [1982]; and A. H. Havelaar et al., "Factors effecting the enumeration of coliphages in sewage and sewage-polluted waters," Antonie van Leewenhoek 49: 387-397 [1983]).

However, the detection limits provided by these methods are no better than those obtained with standard methods for water quality determinations based on coliform analysis. Thus, these methods do not provide a significant advantage over the traditional methods of water analysis.

In summary, the coliform group falls far short of the ideal indicator system. Coliform-free drinking water has been implicated in several waterborne outbreaks [see e.g., B. J. Dutka, "Coliforms are inadequate index of water quality," J. Environ. Health 36: 39-46 [1973]). Likewise, the presence of coliforms in a particular water sample does not necessarily correlate well with the incidence of disease.

Even the enumeration of "feca coliforms" is less than optimal, as some organisms such as Klebsiella are capable of producing positive test results. Such observations led to the development of alternative indicator organisms, including tests specific for *E. coli*, fecal streptococci (e.g., enterococci), Klebsiella, *Clostridium perfringens*, *Pseudomonas aeruginosa*, Bifidobacterium, Bacteroides, *Aeromonas hydrophilia*, *V. parahaemolyticus*, and *C albicans*, as well as other organisms commonly excreted in large numbers by healthy mammals. Notably, various opportunistic and frank pathogens uncommonly associated with waterborne transmission of disease are included in the list of indicator organisms (e.g., *C. perfringens*, *A. hydrolphila*, *V. parahaemolyticus*, and *C albicans*. Although these organisms may be useful in some settings as predictors of waterborne disease, what remains to be developed is a method for the detection and enumeration of pathogens commonly associated with waterborne diarrheal illness.

Detection and identification of Salmonella and Shigella from clinical samples has traditionally involved microbiological cultures, biochemical analyses and in some cases, serotyping methods. The same methods are used to identify suspected Salmonella or Shigella colonies isolated from clinical samples are also usually used for water, food, and other environmental samples. However, these methods are not well-suited to the unique situations associated with environmental samples, where many of the organisms present are stressed and do not perform as expected in clinical testing methods. For example, in the case of Shigella, testing problems arise due to the instability of some biochemical characteristics and antagonism of *E. coli* and *Proteus vulgaris* toward Shigella (Standard Methods, p. 927).

Despite years of regulation and testing, development of a bacterial indicator which is directly related to fecal contamination and/or the presence of pathogens which can cause waterborne disease (Pipes, p. 449) is desirable. Thus, what is needed is a cost-effective method, which is at least as sensitive and specific as traditional methods for the direct detection of pathogens present in clinical, food, water and other environmental samples.

SUMMARY OF THE INVENTION

In one embodiment, the present invention provides a method for amplification of nucleic acid from one or more enteric pathogens comprising the steps of: a) providing a test sample suspected of containing amplifiable nucleic acid one or more one enteric pathogens; b) isolating the amplifiable nucleic acid from the test sample; c) combining the amplifiable nucleic acid with amplification reagents, and at least two primers selected from the group consisting of primers having the nucleic acid sequence set forth in SEQ ID NO:1, SEQ ID NO:2, SEQ ID NO:3, SEQ ID NO:4, SEQ ID NO:6, SEQ ID NO:7, SEQ ID NO:8 and SEQ ID NO:9, to form a reaction mixture; and d) combining the reaction mixture with an amplification enzyme under conditions wherein the amplifiable nucleic acid is amplified to form amplification product. It is particularly contemplated that SEQ ID NOS: 1 and 2 may be combined with SEQ ID NOS: 3 and 4 in order to amplify Salmonella sequences. It is also particularly contemplated that SEQ ID NOS: 6 and 7 may be combined with SEQ ID NOS: 8 and 9 in order to amplify Shigella In a preferred embodiment, the method of the present invention further comprises the step of detecting the amplification product. It is contemplated that this detection will be accomplished by hybridization of the amplification product with a probe having the nucleic acid sequence set forth in SEQ ID NO:5. It is also contemplated that this detection will be accomplished by hybridization of the amplification product with a probe having the nucleic acid sequence set forth in SEQ ID NO:8 or SEQ ID NO:9.

In one embodiment of the present invention, the method utilizes primers capable of hybridizing to nucleic acid from the enteric pathogens Salmonella and Shigella. It is further contemplated that any Salmonella or Shigella species, subspecies, strain or type will be detected by the method of the present invention.

In one embodiment, the test sample is selected from the group comprising sewage, sludge, soil, food, feed, and water. It is therefore contemplated that the test sample comprise any number of sample types, both environmental and clinical.

In an alternative embodiment, the present invention comprises a method for amplification of nueleic acid from a plurality of enteric pathogens comprising the steps of: a) providing a test sample suspected of containing amplifiable nucleic acid of a plurality of enteric pathogens; b) isolating the amplifiable nucleic acid from the test sample; c) combining the amplifiable nucleic acid with amplification reagents, and all of the primers set forth in SEQ ID NO:1, SEQ ID NO:2, SEQ ID NO:6 and SEQ ID NO:7, to form a reaction mixture; d) combining the reaction mixture with an amplification enzyme under conditions wherein the amplifiable nucleic acid is amplified to form amplification products; and e) detecting the amplification products.

In a preferred embodiment of this method the detecting comprises hybridizing the amplification products with the probes having the nucleic acid sequences set forth in SEQ ID NO:5, and SEQ ID NO:8 or SEQ ID NO:9. In another embodiment, the combining conditions comprise a temperature range of 57° C. to 58° C.

In another preferred embodiment, the enteric pathogens detected by this method are Salmonella and Shigella. In one embodiment, the test sample is selected from the group comprising sewage, sludge, soil, food, feed, and water.

The present invention also contemplates a method for amplification of nucleic acid from an enteric pathogen comprising the steps of: a) providing a test sample suspected of containing amplifiable nucleic acid of an enteric pathogens; b) isolating said amplifiable nucleic acid from the test sample; c) combining the amplifiable nucleic acid with amplification reagents, and the primers set forth in SEQ ID NO:1, SEQ ID NO:2, SEQ ID NO:3, and SEQ ID NO:4, to form a reaction mixture; d) combining the reaction mixture with an amplification enzyme under conditions wherein the amplifiable nucleic acid is amplified to form amplification product; and e) detecting said amplification product. In this embodiment, it is contemplated that a the first reaction mixture will be produced with primers of SEQ ID NOS: 1 and 2. It is then contemplated that a portion or aliquot of this first reaction mixture will be again subjected to PCR using the primers of SEQ ID NOS: 3 and 4 in order to produce a second reaction mixture. It is contemplated that only a portion of this first reaction mixture will be necessary for use in the PCR process with the second set of primers. This use of a "portion" of the first reaction mixture provides advantages in that a smaller initial sample volume may be used, as a second round of amplification is involved.

In a preferred embodiment of this method, the detecting comprises hybridizing the amplification product with a probe having the nucleic acid sequence set forth in SEQ ID NO:5. It is particularly contemplated that this probe is labelled. For example, the probe may be labelled with a radioactive or fluorescent compound or any other reporter molecule. In a particularly beneficial embodiment, the conditions comprise a temperature range of 57° C. to 58° C. In another preferred embodiment, the enteric pathogen is Salmonella.

In one embodiment of this invention, the test sample is selected from the group comprising sewage, sludge, soil, food, feed, and water.

In an additional embodiment, present invention also contemplates a method for amplification of nucleic acid from an enteric pathogen comprising the steps of: a) providing a test sample suspected of containing amplifiable nucleic acid of an enteric pathogens; b) isolating said amplifiable nucleic acid from the test sample; c) combining the amplifiable nucleic acid with amplification reagents, and the primers set forth in SEQ ID NO:6, SEQ ID NO:7, SEQ ID NO:8, and SEQ ID NO:9, to form a reaction mixture; d) combining the reaction mixture with an amplification enzyme under conditions wherein the amplifiable nucleic acid is amplified to form amplification product; and e) detecting said amplification product. In this embodiment, it is contemplated that a the first reaction mixture will be produced with primers of SEQ ID NOS: 6 and 7. It is then contemplated that a portion or aliquot of this fast reaction mixture will be again subjected to PCR using the primers of SEQ ID NOS: 8 and 9 in order to produce a second reaction mixture. It is contemplated that only a portion of this first reaction mixture will be necessary for use in the PCR process with the second set of primers. This use of a "portion" of the first reaction mixture provides advantages in that a smaller initial sample volume may be used, as a second round of amplification is involved.

In a preferred embodiment of this method, the detecting comprises hybridizing the amplification product with a probe having the nucleic acid sequence set forth in SEQ ID NO:8 or SEQ ID NO:9. It is particularly contemplated that this probe is labelled. For example, the probe is labelled with a radioactive or fluorescent compound or any other reporter molecule. In this embodiment, the probe may be of the same sequence as one of the primers. In a particularly beneficial embodiment, the conditions comprise a temperature range of 57° C. to 58° C. In another preferred embodiment, the enteric pathogen is Shigella.

The present invention also contemplates a composition comprising one or more isolated and purified nucleic acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

In a preferred embodiment, the composition further comprises an amplifiable nucleic acid of one or more one enteric pathogens, to form a reaction mixture. In one variation of this embodiment, the enteric pathogen is Salmonella. In another variation, the enteric pathogen is Shigella. In yet another embodiment, there is a combination of enteric pathogens, in particular Salmonella and Shigella. It is contemplated that this composition will be of particular value in the detection of these enteric pathogens in such environmental samples as water and sewage.

DESCRIPTION OF THE DRAWINGS

FIG. 2 is a flow chart for isolation of Salmonella from environmental water.

DESCRIPTION OF THE INVENTION

Figure 1:
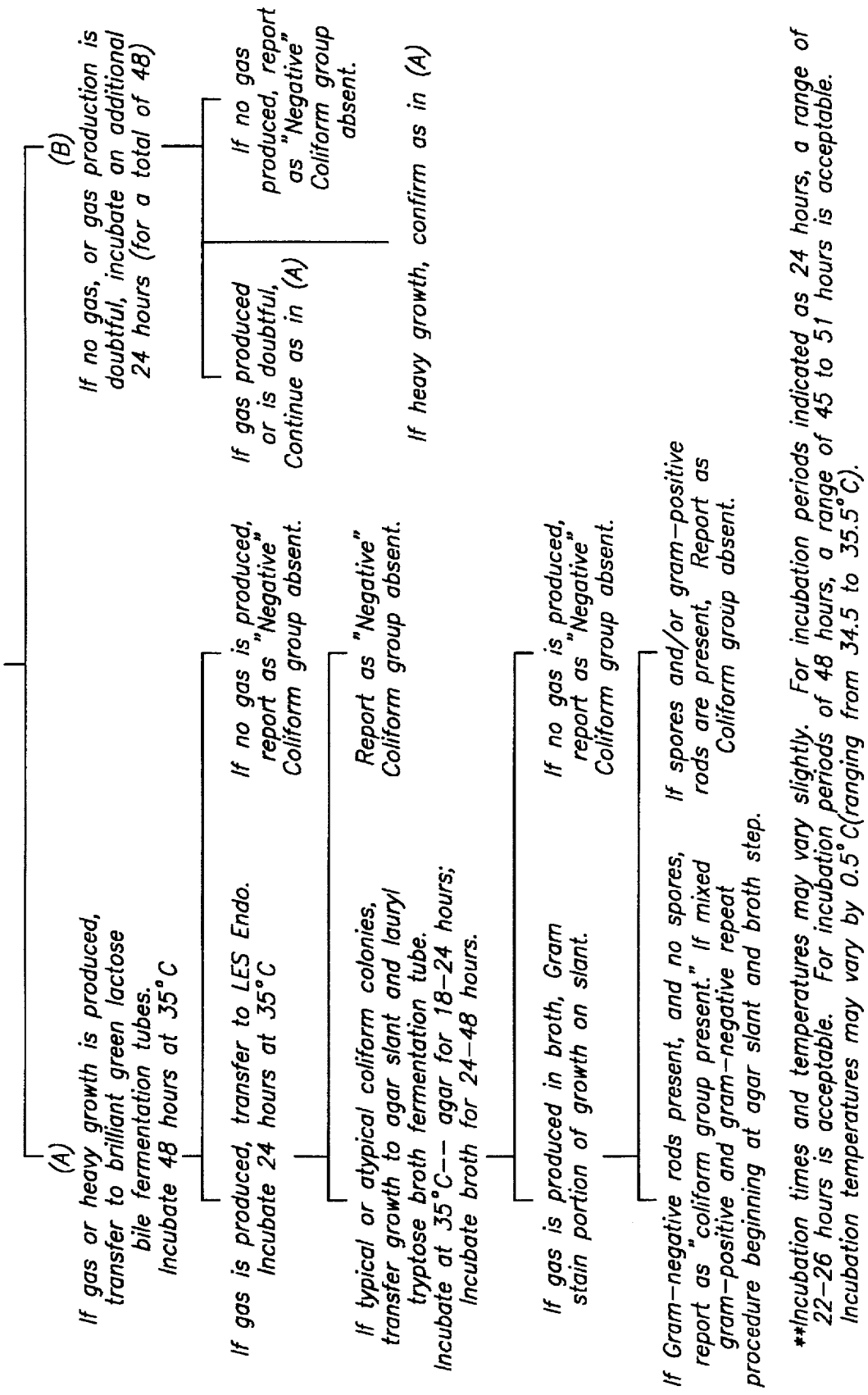
FIG. 1 is a flow chart of the MPN procedure.

The method of the present invention comprises a method for the direct detection of enteric pathogens such as Salmonella and Shigella in environmental and food samples.

Encompassed within this invention are methods for processing samples, including particular assay conditions and/or reagents. Importantly, the reagents and method of the present invention obviate the traditional methods of water quality analysis using indicator bacteria.

In a preferred embodiment, a pair of DNA primers, each 20 base pairs in length is used for the detection of Salmonella in a polymerase chain reaction (PCR) method. In an alternate preferred embodiment, a second pair of primers (19 base pairs each) is used in a nested PCR assay. An additional set of primers (19 base pairs each) was developed for detection of Shigella. The combined use of these primers permits the rapid and specific detection of Salmonella and Shigella.

Importantly, the invention permits the rapid detection of as few as 10 Salmonella organisms in less than five (5) hours. This detection method is both highly sensitive and specific. Importantly, the method of the present invention does not require a pre-culturing step prior to PCR. Thus, the method and reagents of the present invention permit rapid diagnosis of Salmonella and Shigella infection, a concern of great importance in potentially life-threatening diseases (e.g., typhoid) and epidemiologic investigations.

This is also significant for detection of pathogens in water and other samples, especially for organisms such as Shigella with low infective doses. Estimates indicate that as few as 200 organisms is all that is required to produce disease in healthy adults (P. Zwadyk, "Enterobacteriaceae: Salmonella and Shigella, intestinal pathogens," pp. 613–622 in W. K. Joklik et al., (eds), Zinsser Microbiology, 18th edition [Appleton Century Crofts, Norwalk, Conn., 1984]). Thus, exposure to a very few organisms may result in disease. Given the incidence of shigellosis (or "bacillary dysentery"), with approximately 500,000 deaths reported annually (see e.g., Hale, p. 206), detection of this organism is highly desirable.

The rapid, sensitive and specific detection method of the present invention is therefore extremely well-suited for the detection of low numbers of pathogens. Thus, it is contemplated that the present invention be used in various settings, including, but not limited to, such areas as clinical, veterinary, food, dairy, and feed industries, and water quality (e.g., drinking water, as well as sewage treatment).

While some previous reports indicate that molecular methods are useful for the detection of such pathogens as Salmonella and Shigella, none disclose the method nor primers of the present invention. The cumbersome and error-prone methods described by Steffan and Atlas to enhance PCR efficiency with environmental samples are not necessary with the present invention. (R. J. Steffan and R. M. Atlas, "Polymerase chain reaction: Applications in environmental microbiology," Ann. Rev. Microbiol., 45: 137–161 [1991].) For example, there is no need to dilute the sample after the first few cycles of PCR, nor is there the need to dilute the sample after a completed reaction sequence and then perform an additional round of amplification (see Steffan and Atlas p. 141 for a description of this procedure). Nor is there the requirement that the primer concentration be changed during the PCR cycling, as recommended by some authors (see Steffan and Atlas, p. 141 for a description).

Two publications describe the same 1.8 kb HindIII fragment from the chromosomal DNA of *Salmonella typhimurium*, portions of which were used to develop probes for the detection of Salmonella in foods and other samples (Tsen et al., "DNA sequence of a Salmonella-specific DNA fragment and the use of oligonucleotide probes for Salmonella detection," Appl. Microbiol. Biotechnol., 35: 339–347 [1991], and Tsen et al., "Possible use of a 1.8 kb DNA fragment for the specific detection of Salmonella in foods," J. Ferment. Bioeng. 68: 1–6 [1989]). Unlike the present invention, Tsen et al. did not utilize PCR. Rather, their detection methods were based solely on nucleic acid hybridization (i.e., probe) technology.

Interestingly, while Tsen examined the specificity of six probes having sequences within this 1.8 kb fragment, only three were found to be "highly specific" for Salmonella. The other three probes (TS1, TS2 and TS3) were found unsuitable because false positive reactions were sometimes observed with *E. coli* and Citrobacter. This cross-reactivity was not observed with the present invention.

Definitions

The terms "sample" and "specimen" in the present specification and claims are used in their broadest sense. These terms are also used interchangeably. On the one hand they are meant to include a specimen or culture. On the other hand, they are meant to include both biological and environmental samples. In addition, a "sample" may or may not contain nucleic acid. Furthermore, it may or may not contain "sample template" and/or "background template."

Biological samples may be animal, including human, fluid or tissue, food products and ingredients such as dairy items, vegetables, meat and meat by-products, and waste. Environmental samples include environmental material such as surface matter, soil, water, wastewater, sewage, sludge, industrial samples (e.g., industrial water), as well as samples obtained from food and dairy processing instruments, apparatus, equipment, disposable and non-disposable items. Also included are samples obtained from animals which live in fresh, brackish and/or seawater (e.g., shellfish, fish, and marine animals). In addition to these "environmental" samples, it is contemplated that "drinking water" will be used with the method of the present invention. It is intended that the term "drinking water" encompass all types of water used for consumption by humans and other animals, including but not limited to well water, run-off water, water stored in reservoirs, rivers, streams, etc. These examples are not to be construed as limiting the sample types applicable to the present invention.

The terms also encompass all types of samples obtained from humans and other animals, including but not limited to, body fluids such as urine, blood, fecal matter, and cerebrospinal fluid (CSF), as well as solid tissue. Also included are swabs and other sampling devices which are commonly used to obtain samples for culture of microorganisms. These human and veterinary samples are included within the term "clinical" samples.

Whether biological or environmental, a sample suspected of containing microorganisms may or may not first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention to, following subjecting a sample to a conventional enrichment means, subjecting the resultant preparation to further purification such that pure or substantially pure cultures of a strain of a species of interest are produced.

As used herein, the term "organism" is used to refer to any species or type of microorganism, including but not limited to bacteria, viruses, fungi, and protozoans.

As used herein, the term "culture" refers to any sample or specimen which is suspected of containing one or more microorganisms. "Pure cultures" are cultures in which the organisms present are only of one genus and species. "Mixed cultures" are cultures in which more than one genus and/or species of microorganism are present.

As used herein, the terms "microbiological media" and "culture media," and "media" refer to any substrate for the growth and reproduction of microorganisms. "Media" may be used in reference to solid plated media which support the growth of microorganisms. Also included within this definition are microbial growth systems which incorporate living host organisms, as well as any type of media. Such systems include, but are not limited to the cell culture systems utilized to grow various fastidious organisms As used herein, the term "selective media" refers to media which support the growth of particular organisms of interest but inhibit other organisms. Such inhibition may result due to medium constituents such as compounds which are selectively toxic, as well as the end-products of microbial metabolism produced by organisms which utilize the medium constituents.

As used herein, the term "differential media" refers to media which support the growth of various organisms, but permit visual differentiation between the different genera or species.

As used herein, the term "primary isolation" refers to the process of culturing organisms directly from the sample. Thus, primary isolation involves such processes as inoculating an agar plate from a culture swab, water sample, etc. Primary isolation may also be done in liquid or semi-solid media.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism based on observation such as colony characteristics, growth on primary isolation media, gram stain results, etc.

As used herein, the term "definitive diagnosis" is used to refer to a final diagnosis in which the etiologic agent of the patient's disease has been identified. As used herein, this term is also applicable to the identification of organisms present in environmental samples.

As used herein, the term "base" refers to a monomeric unit of nucleic acid. Technically, the monomeric units of DNA are termed "deoxyribonucleotides" and those of RNA are "ribonucleotides." Each nucleotides is comprised of: 1) a nitrogenous heterocyclic base, 2) a pentose, and 3) a molecule of phosphoric acid. Since the nucleotide is distinguished by the type of base, a shorthand reference for nucleotides has evolved—the nucleotide is simply referred to as a "base."

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nueleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, and incorporated by reference, the term "polymerase chain reaction" ("PCR") refers to the method of K. B. Mullis U.S. Pat. Nos. 4,683,195 and 4,683,202, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogenous mixture of nucleic acid. For example, in the case of Qβ replicase, MDV-1 RNA is the specific template for the replicase. D. L. Kacian et al., Proc. Nat. Acad. Sci USA 69: 3038 (1972). Other nucleic acid will not be replicated by this amplification enzyme. Similarly, in the case of T7 RNA polymerase, this amplification enzyme has a stringent specificity for its own promoters. M. Chamberlin et al., Nature 228: 227 (1970). In the case of T4 DNA ligase, the enzyme will not ligate the two oligonucleotides where there is a mismatch between the oligonucleotide substrate and the template at the ligation junction. D. Y. Wu and R. B. Wallace, Genomics 4: 560 (1989). Finally, Taq polymerase, by virtue of its ability to function at high temperature, is found to display high specificity for the sequences bounded and thus defined by the primers; the high temperature results in thermodynamic conditions that favor primer hybridization with the target sequences and not hybridization with non-target sequences. PCR Technology, H. A. Erlich (ed.) (Stockton Press 1989).

Some amplification techniques take the approach of amplifying and then detecting target; others detect target and then amplify probe. Regardless of the approach, nucleic acid must be free of inhibitors for amplification to occur at high efficiency.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR. K. B. Mullis, et al., Cold Spring Harbor Symposia, Vol. II, pp. 263–273 (1986). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. Advantages to the use of nested primers include the large degree of specificity, as well as the fact that a smaller sample portion may be used and yet obtain specific and efficient amplification.

As used herein, the term "multiplex" is used in reference to amplification of multiple nucleic acid sequences (e.g., PCR procedures which include multiple primer sets to simultaneous amplify nucleic acids from multiple sources). In multiplex PCR, specific, sensitive and distinguishable simultaneous amplification of gene sequences from different organisms (e.g., Salmonella and Shigella) may be conducted. Because more than one organism may be detected and identified in multiplex reactions, this procedure may provide significant advantages over single PCR methods in which only one gene sequence is detected.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the terms "polymerase inhibitors," and "interfering" compounds or "substances" include all compounds (organic and inorganic) that reduce the amount of nucleic acid replication by enzymes. It is not intended to be limited by the mechanism by which these inhibitors or interfering compounds achieve this reduction. Furthermore, it is not intended to be limited to only those inhibitors which display large reductions.

It is contemplated that methods to avoid problems associated with "carryover" will by used in conjunction with the present invention. As used herein, the term "carryover" is broadly defined as nucleic acid that is accidentally introduced into a reaction mixture. Of course, the types of accidental introductions are numerous. Nucleic acids can be introduced during a spill or because of poor laboratory technique (e.g., using the same reaction vessel or the same pipette twice). However, of greater concern is the introduction of nucleic acids that occurs even during normal laboratory procedures, including inadvertent transfer from contaminated gloves.

It is contemplated that any of the various approaches to controlling carryover reported in the literature will be used with the present invention, including containment, elimination, prevention, and/or "sterilization" (both post-amplification sterilization, as well as pre-amplification sterilization). For example, the "sterilization" methods as those described in U.S. Pat. No. 5,139,940 issued to Isaacs et al., and U.S. Pat. No. 5,221,608 issued to Cimino et al., are hereby incorporated by reference and may be used with the present invention.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \ G+C)$, when a nucleic acid is in aqueous solution at 1M NaCl (see e.g., Anderson and Young, Quantitative Filter Hybridisation, in *Nucleic Acid Hybridisation* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "detection" is used in reference to the observation of a product of interest. Detection may refer to isolation of organisms on media, or it may refer to visualization or the recognition of the presence of certain nucleic acids. For example, the PCR products produced in the present invention may be "detected." Detection may be achieved through various methods, including the use of "reporter compounds," including radiolabels, fluorescence, luminescence or enzymatically-labelled compounds. The efficiency of detection is largely dependent upon the "sensitivity" and "specificity" of the methods employed. As used herein, the term "sensitivity" is used in reference to the ability of the method to detect the item or compound of interest when it is present (i.e., detection of "true positives"). As used herein, the term "specificity" is used in reference to the ability of the method to detect the particular item or compound or interest, but without detecting other compounds or items (i.e., not detecting "false positives"). Thus, the greater the specificity, fewer "cross-reactions" will be observed. For example, in nucleic acid detection methods, only the particular sequence of interest and no other is detected in a method that is highly specific. If the method is sensitive, all of the sequences of interest are detected. Thus, it is clear that the optimal methods of detection will be both highly sensitive and highly specific.

It is also contemplated that various detection formats will be utilized with the present invention, including gels of any composition, beads, immobilized reactants, etc. It is not intended that the method of the present invention be limited to a particular detection system or format.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g or gm (grams); mg (milligrams); μg (micrograms); ng (nanograms); l or L (liters); ml (milliliters); μl (microliters); cm (centimeters); mm (millimeters); μm (micrometers); nm (nanometers); °C. (degrees Centigrade); CFU (colony forming units); SDS (sodium dodecyl sulfate); PBS (phosphate buffered saline; 137 mM NaCl, 2.7 KCl, 8.1 mM $Na_2HPO_4$, 1.5 mM $KH_2PO_4$; pH 7.3); SSC (0.15M NaCl, 0.015 trisodium citrate; pH 7.0); TE buffer (10 mM Tris-HCl, 1.0 mM EDTA; pH 8.0); PCR buffer (an aqueous solution of 10 mM Tris-HCl, 50 mM KCl, and 1.5 mM $MgCl_2$, pH 8.3); reaction mixture (1× strength PCR buffer, 200 μM of each deoxynucleoside triphosphate [i.e., dNTP's—dATP, dTTP, dCTP, and dGTP], 0.3 μM of each primer, and 0.5 μl Taq DNA polymerase [Perkin-Elmer] per 100 μl solution); ELISA (Enzyme-Linked Immunosorbent Assay); Millipore (Millipore, Bedford, Mass.; Pharmacia (Pharmacia Fine Chemicals, Piscataway, N.J.); BIO 101 (BIO 101 Inc., La Jolla, Calif.); Difco (Difco Laboratories, Detroit, Mich.); Amicon (Amicon, Beverly, Mass.); Applied Biosystems (Applied Biosystems International, Foster City, Calif.); Perkin Elmer (Perkin-Elmer, Norwalk, Conn.); FMC BioProducts (FMC BioProducts, Rocklane, Me.); BioVentures (BioVentures, Inc., Murfreesboro, Tenn.); UVP (Ultra Violet Products, San Gabriel, Calif.); Amersham (Amersham, Arlington Heights, Ill.); Stratagene (Stratagene, La Jolla, Calif.); Scientific Products (McGraw Park, Ill.); Sigma (Sigma Chemical Co., St. Louis, Mo.); ATCC (American Type Culture Collection, Rockville, Md.); Boehringer Mannheim (Boehringer Mannheim, Indianapolis, Ind.); Eastman Kodak (Eastman Kodak, Rochester, N.Y.); DOH (Department of Health, Honolulu, Hi.); MPN (most probable number); MF (membrane filtration). A Perkin-Elmer GeneAmp™ PCR system 9600 was used for all of the PCR reactions.

The following table lists the species, number of isolates and sources of the organisms used in the following examples. The organisms used in the development of the present invention were obtained from a variety of sources. Importantly, in addition to type cultures and lab-adapted strains, the present invention was developed using environmental isolates as well. All Salmonella isolates obtained from the Hawaii Department of Health were isolated from clinical samples and were serotyped. All of these isolates were grown in heart infusion (Difco Laboratories, Detroit, Mich.) for 24 hrs at 37° C.

TABLE 3

| Organism | # of Isolates Tested | Source |
|---|---|---|
| Salmonella typhimurium | 1 | ATCC 14028 |
| Salmonella typhimurium | 5 | DOH, Honolulu, HI* |
| Salmonella bredeney | 1 | DOH, Honolulu, HI* |
| Salmonella heidelberg | 1 | DOH, Honolulu, HI* |
| Salmonella infantis | 1 | DOH, Honolulu, HI* |
| Salmonella sandiego | 1 | DOH, Honolulu, HI* |
| Salmonella muenchen | 1 | DOH, Honolulu, HI* |
| Salmonella anatum | 2 | DOH, Honolulu, HI* |
| Salmonella hadar | 2 | DOH, Honolulu, HI* |
| Salmonella agona | 1 | DOH, Honolulu, HI* |
| Salmonella tuebingen | 1 | DOH, Honolulu, HI* |
| Salmonella cerro | 1 | DOH, Honolulu, HI* |
| Salmonella give | 1 | DOH, Honolulu, HI* |
| Salmonella alachua | 1 | DOH, Honolulu, HI* |
| Salmonella weltevreden | 12 | DOH, Honolulu, HI* |
| Salmonella newport | 4 | DOH, Honolulu, HI* |
| Salmonella lanka | 3 | DOH, Honolulu, HI* |
| Salmonella oslo | 7 | DOH, Honolulu, HI* |
| Salmonella singapore | 1 | DOH, Honolulu, HI* |
| Salmonella nottingham | 1 | DOH, Honolulu, HI* |
| Salmonella tennessee | 1 | DOH, Honolulu, HI* |
| Salmonella montevideo | 1 | DOH, Honolulu, HI* |
| Salmonella stanley | 1 | DOH, Honolulu, HI* |
| Salmonella houten | 2 | DOH, Honolulu, HI* |
| Salmonella derby | 1 | DOH, Honolulu, HI* |
| Salmonella cubana | 1 | DOH, Honolulu, HI* |
| Salmonella dublin | 1 | DOH, Honolulu, HI* |
| Escherichia coli | 1 | ATCC 25922 |
| Escherichia coli | 1 | ATCC 35401 |
| Escherichia coli | 1 | ATCC 43886 |
| Escherichia coli | 1 | ATCC 43889 |
| Escherichia coli | 1 | ATCC 43890 |
| Escherichia coli | 1 | ATCC 43894 |
| Escherichia coli | 1 | ATCC 43895 |
| Escherichia coli | 1 | ATCC 43896 |
| Enterobacter aerogenes | 1 | ATCC 13048 |
| Citrobacter freundii | 1 | ATCC 8090 |
| Klebsiella pneumoniae | 1 | ATCC 13883 |
| Shigella flexneri | 1 | ATCC 12022 |
| Shigella sonnei | 1 | ATCC 25931 |
| Bacillus cereus | 1 | ATCC 14579 |
| Bacillus subtilis | 1 | ATCC 6051 |
| Pseudomonas aeruginosa | 1 | ATCC 27853 |
| Staphylococcus aureus | 1 | ATCC 25923 |
| Streptococcus faecalis | 1 | ATCC 29212 |
| Acinetobacter calcoaceticus | 1 | ATCC 19606 |
| Serratia marcescens | 1 | ATCC 8100 |
| Streptococcus pyogenes | 1 | ATCC 19615 |
| Enterobacter cloacae | 1 | ATCC 23355 |
| Proteus vulgaris | 1 | ATCC 13315 |
| Staphylococcus epidermidis | 1 | ATCC 12228 |

EXAMPLE 1

Collection of Environmental Samples

Environmental samples were collected in twenty liter volumes from the area near the Sand Island, Oahu treatment facility's outfall. This outfall is located 9000 ft from shore and is at a depth of 243 ft. Environmental samples were also collected in 20 liter volumes from Manoa Stream, a fresh water urban drainage system which serves the Honolulu suburbs.

FIG. 2 is a flow chart illustrating the steps used to isolate Salmonella from these samples. Briefly, a 15 tube MPN set up (5 tubes each of 10 ml, 1 ml, and 0.1 ml) in tetrathionate broth (Difco) (see e.g., *Standard Methods*, pp. 880-882, for a description of the procedure) was inoculated with either sample water (with no concentration) or water concentrated in a Membrex concentrator, and incubated for 24 hrs at 37° C. Tubes showing growth after 24 hrs were streaked on xylose lysine deoxycholate agar ("XLD"; (Difco) and Hektoen enteric agar ("HE"; Difco) and incubated for 24 hrs at 37° C. Characteristic Salmonella-like colonies were then inoculated on triple iron agar ("TSI"; Difco) and lysine iron agar ("LIA"; Difco) slants. The identification of isolates with correct growth characteristics on TSI and LIA (i.e., for most Salmonella strains, glucose, but not lactose nor sucrose fermentation, along with gas and $H_2S$ production in TSI, and lysine decarboxylation in LIA slants) were confirmed with polyvalent antisera specific for Salmonella O-group antigens (Set A-1, Difco).

EXAMPLE 2

Extraction, Purification and Concentration of DNA

Mid-log-phase pure cultures were washed twice with phosphate-buffered saline (PBS), and DNA extraction was performed using the GNOME DNA isolation kit, (BIO 101), according to the protocol provided by the manufacturer.

Sewage samples were processed using the method of A. K. Bej et al., "Polymerase chain reaction-gene probe detection of microorganisms by using filter-concentrated samples," Appl. Environ. Microbiol., 57: 3529-3534 (1991). Briefly, this in this protocol, portions (10 ml) of samples and dilutions in PBS were filtered through 0.5 µm pore-size FHLP Teflon filters with 13 mm diameters (Millipore) in a Swinnex filter holder (Millipore). This preparation was then used as the source for the total DNA, which extracted from the samples by a rapid freeze-thaw. In this process, the samples were placed in a dry ice and ethanol bath for 1 minute and a 50° C. water bath for 1 minute, and the cycle repeated five times.

The samples were then loaded onto a Sephadex G-200 (Pharmacia) column which was then centrifuged twice for 10 mins. each time at 1,100× g to obtain 100 µl of eluent. Approximately 1.5 ml of sterile deionized water was added to this final volume. Purified DNA was then concentrated using an Amicon Centricon concentrator to a final volume of 20 µl. These DNA preparations were then used in the PCR protocols described below.

For environmental water samples, the same filtration process was used as described for sewage. However, rather than the freeze-thaw step, these samples were purified by a modification of a previously described method (Y.-L Tsai and B. H. Olson, "Rapid methods for separation of bacterial DNA from humic substances for polymerase chain reaction," Appl. Environ. Microbiol., 58: 2292-2295 [1991]; and Y.-L Tsai et al., "Detection of *Escherichia coli* in sewage and sludge by polymerase chain reaction," Appl. Environ. Microbiol., 59: 353-357 [1993]). Briefly, 200 µl of the crude extract was placed in 200 µl of a solution comprising 20% w/v Chelex anion exchange resin suspended in 10 mM Tris-HCl, pH 8.0, 1.0 mM EDTA, and 0.1% sodium azide. This suspension was boiled for 10-12 min., and loaded onto a Sephadex G-200 (Pharmacia) column which was then centrifuged twice for 10 mins. each time at 1,100× g to obtain 100 µl of eluent. Purified DNA was then concentrated in the presence of sterile deoinized water, as described above, using an Amicon Centricon concentrator to a final volume of 20 µl.

Although it was not usually found to be necessary, the Sephadex G-200 column was also found to be useful for environmental water with a large amount of suspended material.

These sewage and environmental water preparations were then used in the PCR protocols described below.

EXAMPLE 3

Development of PCR Protocols

This experiment describes the development and production of the primers utilized in the present invention.

Multiple primers were developed, including primer BR-SALa (SEQ ID NO:1) and BR-SALb (SEQ ID NO:2), which were prepared from a previously published Salmonella restriction fragment sequence (Tsen et al., 1991). A second nested primer set SAL-Ia (SEQ ID NO:3) and SAL-Ib (SEQ ID NO:4) was also prepared from the same large sequence. These primers are shown in Table 4. As shown in Table 5, primer set BR-SALa and BR-SALb generated a 526 bp PCR product and nested primer set SAL-Ia and SAL-Ib corresponded to a 282 bp PCR product. These primers were produced with an automatic DNA synthesizer (ABI 381A; Applied Biosystems).

TABLE 4

Primers Used For Detection Of Salmonella

| Primer | Sequence | SEQ ID NO: |
|---|---|---|
| BR-SalA | 5'-ACG GTT GTT TAG CCT GAT AC-3' | SEQ ID NO:1 |
| BR-SalB | 5'-CTG GAT GAG ATG GAA GAA TG-3' | SEQ ID NO:2 |
| BR-Sal IA | 5'-GTT CGG CAT TGT TAT TTC T-3' | SEQ ID NO:3 |
| BR-Sal IB | 5'-CTC AGG GTC ATC GTT ATT C-3' | SEQ ID NO:4 |

TABLE 5

Position And Products Produced By The Primers Used In The PCR Detection Of Salmonella

| Primer Set | Sequence position* | Product length (bp) |
|---|---|---|
| BR-SALa | 1124–1144 | 526 |
| BR-SALb | 1630–1650 | |
| SAL-Ia | 1280–1299 | 282 |
| SAL-Ib | 1543–1562 | |

*Position of primers within the 1.8-kb Salmonella DNA sequence (Tsen et al., 1991).

EXAMPLE 4

Hybridization of PCR Products

Following PCR amplification, DNA electrophoresis and hybridization methods were used to confirm the sequences of the PCR products. In this experiment, the DNA samples were run through the PCR protocol and then electrophoresed in on a 2% SeaKem GTG agarose (FMC BioProducts). In most experiments, a λ-HindIII digest (Sigma) was used as a marker (usually in lane 1). In other experiments, the "Biomarker-low" obtained from BioVentures was used as a marker lane. The gel was then stained with ethidium bromide (0.5 µg/l) and DNA bands were observed using a model 6–63 transilluminator (UVP).

For Salmonella, an internal probe, "TS21" with the sequence 5'-TACATCGTAAAGCACCATCGCAAAT-3' (SEQ ID NO:5) chosen from among a large previously published sequence, was then used to confirm the identity of the PCR products. For Shigella, two internal probes, with the sequences 5'-AGCAGTCTTTCGCTGTT-3 (SEQ ID NO:8) and 5'-AAACGCATTTCCTTCAC-3' (SEQ ID NO:9) were used interchangeably as probes. These Shigella sequences were used both as probes and as primers in a nested primer PCR protocol to detect Shigella. These sequences were chosen from among a large previously published sequence (A. B. Hartman et al., "Sequence and molecular characterization of a multicopy invasion plasmid antigen gene, ipaH, of Shigella flexneri, J. Bacteriol., 172: 1905–1915 [1990]).

The probe oligonucleotides were 3' labeled with digoxigenin-11-dUTP, using a Genius 5 nonradioactive DNA labeling kit (Boehringer Mannheim) per the manufacturer's directions. PCR products were transferred onto Hybond-N+ positively charged nylon membranes (Amersham) using a PosiBlot pressure blotter (Stratagene) for Southern analysis (E. M. Southern, "Detection of specific sequences among DNA fragments separated by gel electrophoresis," J. Mol. Biol., 98: 503–517 [1975]). DNA was fixed to the nylon membranes by UV irradiation at 254 nm for 2 min using a CL-1000 ultraviolet crosslinker (UVP).

Hybridization was performed at 55° C. in presence of a labeled oligonucleotide internal probe (2 pmol/ml). The hybridized filters were washed twice with a high-salt solution (2× SCC in 0.1% SDS) at 50° C. A Genius 3 nucleic acid detection kit (Boehringer Mannheim) was used to prepare the hybridized filters for chemiluminescent detection. The hybridization signals were visualized on X-OMAT (Eastman Kodak) using autoradiography as described by Sambrook et al., Molecular Cloning: A Laboratory Manual, 2d ed., Cold Spring Harbor Laboratory, Cold Spring Harbor, N.Y. (1989).

EXAMPLE 5

Optimization of PCR Conditions

A series of experiments were conducted in which various parameters were tested in the PCR protocol to fine-time the procedure to amplify Salmonella, but not E. coli DNA.

The template DNA was obtained from Salmonella or E. coli as described in the previous examples. In these experiments, a λ-HindIII digest (Sigma) was included as a marker. All samples were processed in a single (i.e., not nested) primer PCR for thirty cycles, although at varying temperatures as described below:

Experiment 1

In this experiment, two S. typhimurium isolates (lanes 2 and 3), S. heidelberg (lane 4), S. bredeney (lane 5), E. coli 890 (lane 7), E. coli 894 (lane 8), E. coli 889 (lane 9), and E. coli S1-3 (lane 10) were tested. Lane 1 contained the λ-HindIII ("HindIII") digest as marker. The two primers, BR-SALb and BR-SALa were used in each of these experiments.

Figure 3:
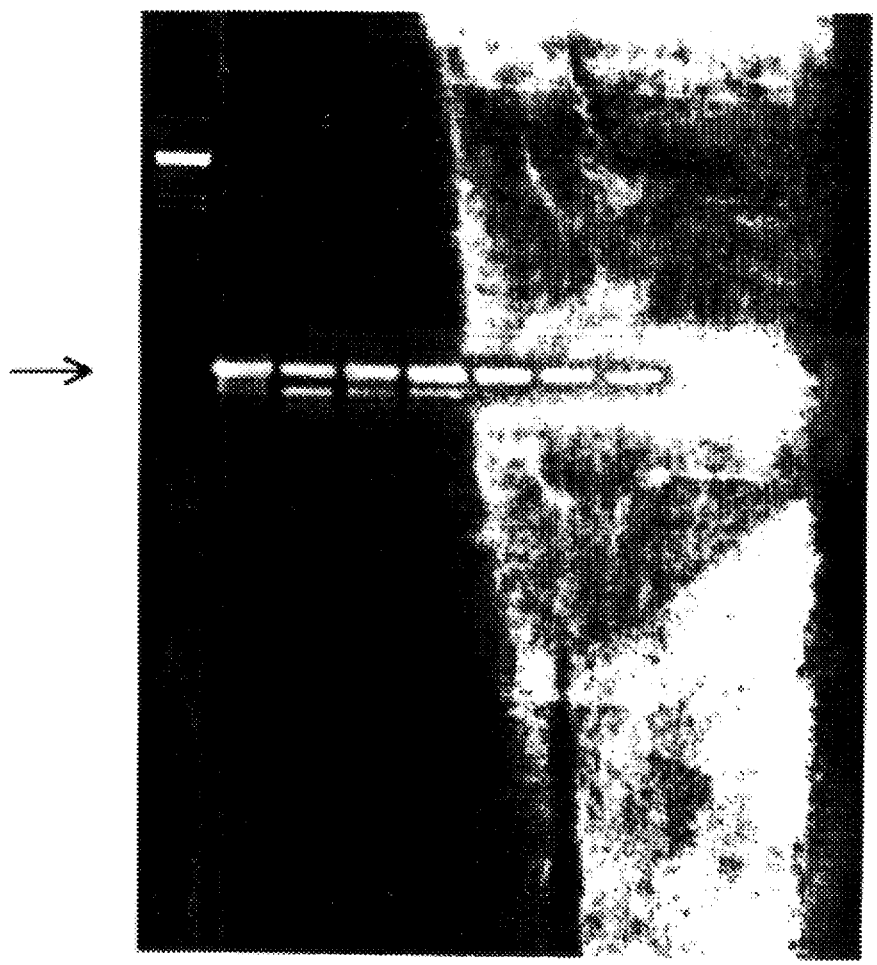
FIG. 3 is a gel showing amplification of Salmonella and E. coli.

First, low annealing temperatures were tested. Following the initial 94° C. 5 minute exposure, the samples were cycled at 94° C. for 2 min., 53.5 for 1 min., and 72.0° C. for 1 min. At these cycling conditions, all of the samples were amplified. These results are shown in FIG. 3, with the arrow showing the band of interest. As shown in this figure, there are multiple bands present in the HindIII lane, (lane 1) as well as multiple bands in the Salmonella lanes (lanes 2–9), and PCR product present in the E. coli lanes (lanes 8–10; very faint bands appear to be barely visible in lanes 9–10).

Experiment 2

Figure 4:
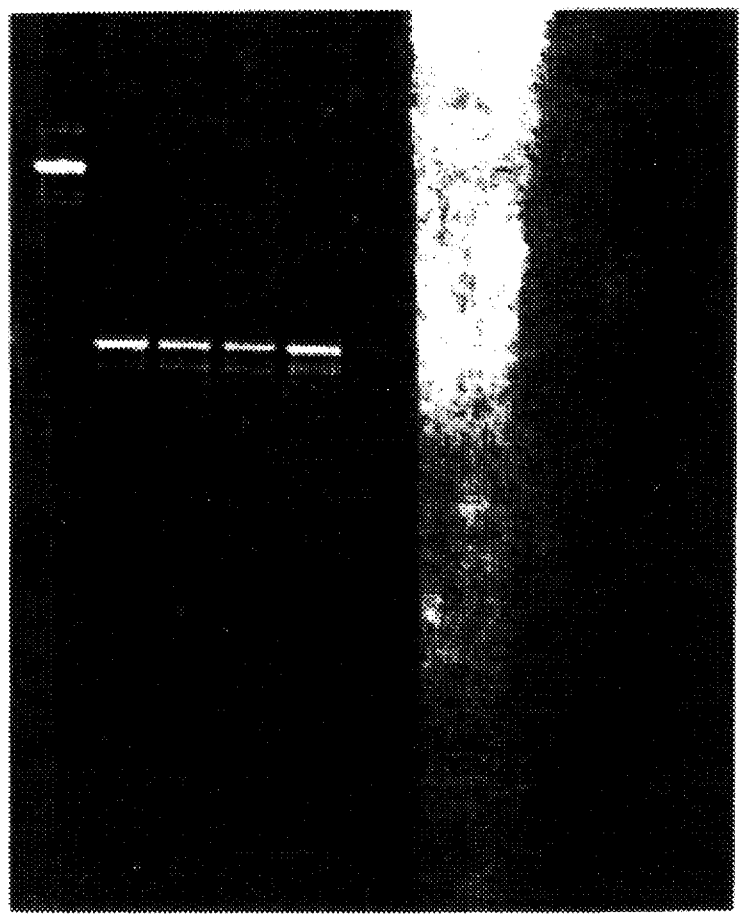
FIG. 4 is a gel showing amplification of Salmonella and E. coli.

In the next run, the cycling parameters were adjusted to 94° C. for 2 min., 55.5° C. for 1 min., and 72.0° C. for 1 min. The same lane configuration was used as described above for Experiment 1. As shown in FIG. 4, these conditions resulted in the production of multiple bands in the HindIII lane, as well as multiple bands in the Salmonella lanes, and very faint PCR products present in the E. coli lanes as well.

Experiment 3

Figure 5:
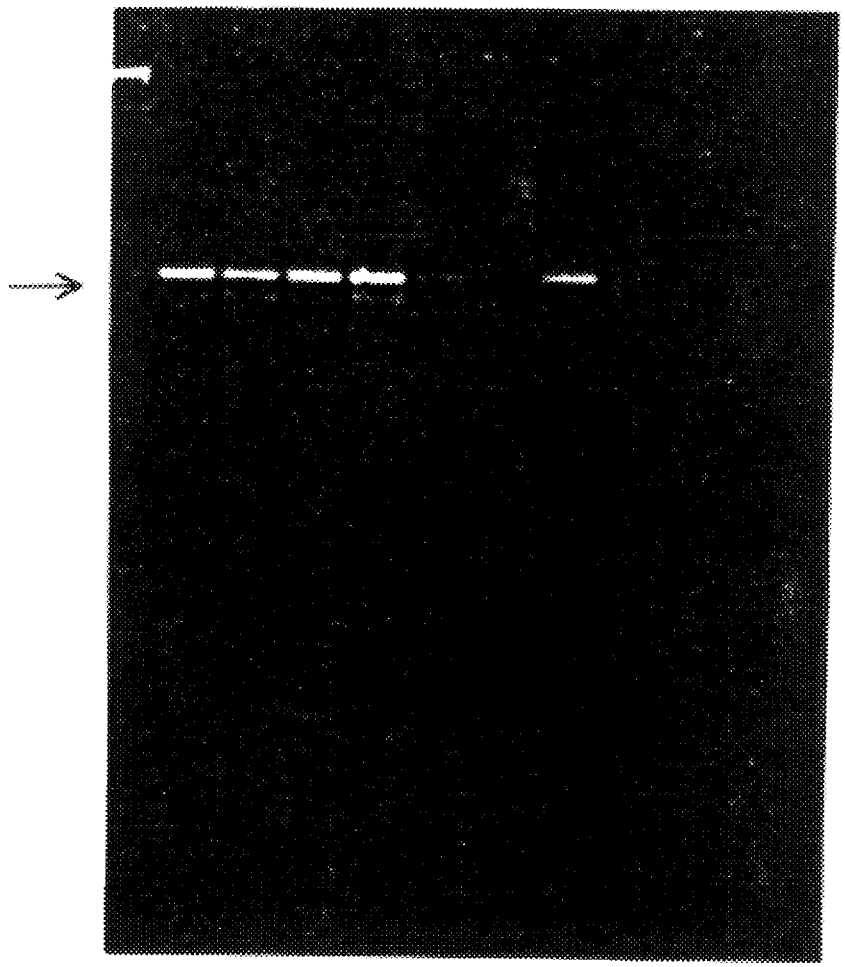
FIG. 5 is a gel showing amplification of Salmonella and E. coli.

Because these low annealing temperatures produced unsatisfactory results, higher temperatures were then tested. The same lane configuration was again used, with the exception that lanes 9–10 were empty. In this run, the mixtures were exposed to thirty cycles of 94° C. for 2 min., 56.5° C. for 1 min., and 72.0° C. for 1 minute. The PCR products were then run on gels and visualized. FIG. 5 shows the results for this experiment. As shown in this Figure, although there was good amplification of Salmonella there also was detectable amplification of some *E. coli* strains, again indicating that the reaction conditions were not sufficiently stringent to produce specific results.

Experiment 4

Figure 6:
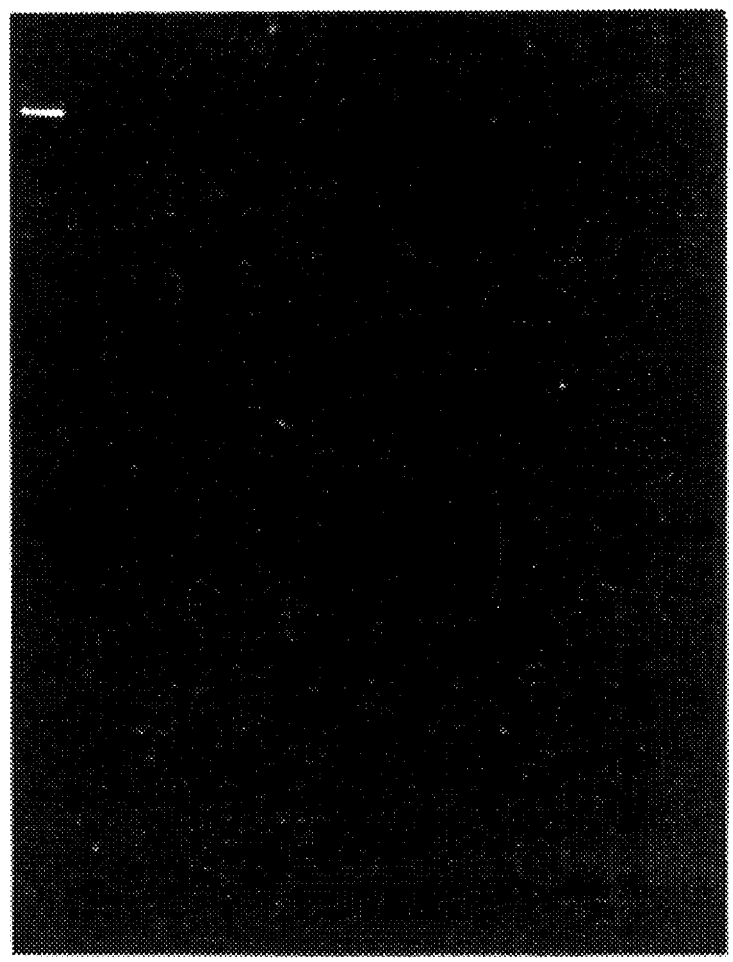
FIG. 6 is a gel showing amplification of Salmonella and E. coli.

Higher temperatures were then used in the PCR, in an attempt to increase the specificity of the reaction. In this run, the samples were exposed to 30 cycles of 94° C. for 2 min., 58.5° C. for 1 min., and 72.0° C. for 1 min. As described above, the reaction products were run on gels and visualized, with the same lane configurations as described in Experiment 3. As shown in FIG. 6, there was no amplification of Salmonella nor *E. coli*, indicating that the reaction conditions were too stringent to produce results. The only band observed was present in the control HindIII lane.

Experiment 5

Figure 7:
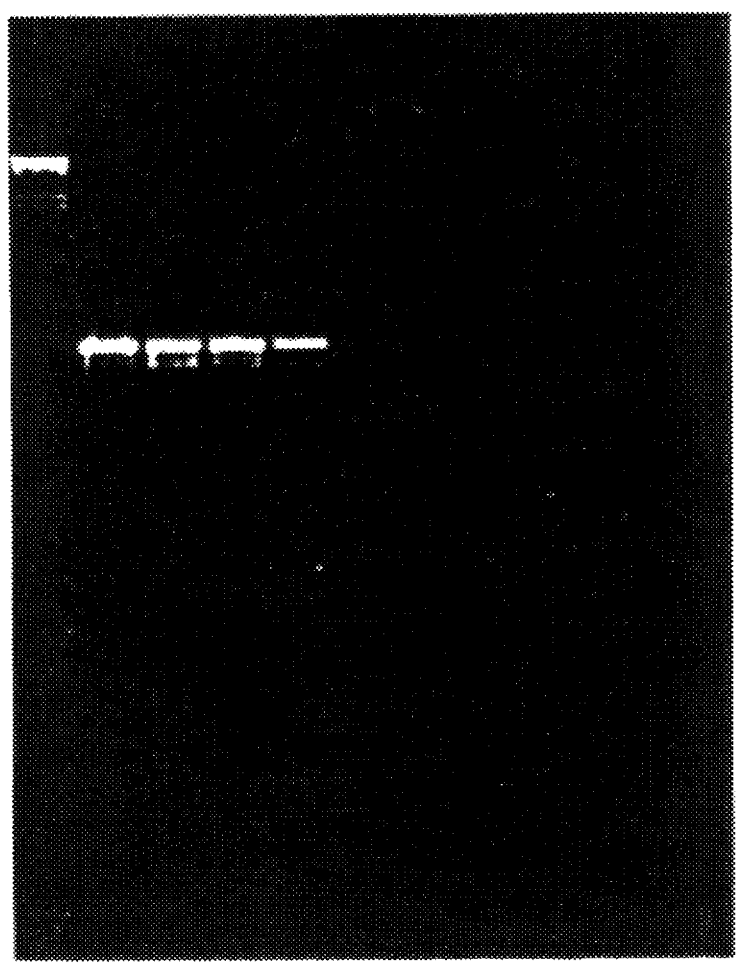
FIG. 7 is a gel showing amplification of Salmonella and E. coli.

Next, the cycling temperatures were again changed used in the PCR, in an attempt to provide optimal sensitivity and specificity in the reaction. In this run, the samples were run in 30 cycles of 94° C. for 2 min., 57.0° C. for 30 sec., and 72.0° C. for 1 min. Again, as described above, the reaction products were run on gels and visualized, with the same lane configurations as described in Experiment 3. As shown in FIG. 7, there was good amplification of Salmonella, but no amplification of *E. coli*. However, the bands produced by the Salmonella PCR products were not clear and sharply distinct.

Experiment 6

Figure 8:
FIG. 8 is a gel showing amplification of Salmonella and E. coli.

In a final run, the annealing temperature was again changed, in an attempt to provide optimal sensitivity and specificity in the reaction. In this run, the samples were run for 30 cycles of 94° C. for 2 min., 57.5° C. for 30 sec., and 72.0° C. for 1 min. As described above, the reaction products were run on gels and visualized with the same lane configurations as described in Experiment 3. As shown in FIG. 8, there was good amplification of Salmonella, with sharp and distinct bands, but with no amplification of *E. coli*. Thus, these conditions appear optimal for amplification of Salmonella DNA, without amplifying *E. coli* DNA as well.

EXAMPLE 6

Seeding of Sewage and Sludge With Salmonella

Various isolates were used in seeding experiments, in which environmental waters such as sewage and sludge were spiked with known quantities of organisms. For these seeding experiments, mid-log-phase *Salmonella typhimurium* (ATCC 14028) were collected, washed twice with phosphate-buffered saline, and serially diluted ($10^{-2}$ to $10^{-9}$). Plate counts (see e.g., *Standard Methods*, pp. 886–889) were performed on these serial dilutions spread on Hektoen enteric agar (Difco), to determine the number of viable Salmonella in the sample.

The serial dilutions were then seeded into samples of primary treated sewage. Nine ml of sewage were placed in each of six tubes. To these six tubes, 1 ml of diluted organism suspension was added. The samples were mixed well and filtered through a Swinnex filter fitted with an FHLP filter (Millipore). The filtrate was then placed in a microfuge tube, to which 500 µl of sterile water was added. The samples were placed at 85° C. for 5 min., vortexed, and then freeze-thawed. In the freeze-thaw sequence, samples were first frozen in dry ice for five minutes, then thawed at 65° C. for five minutes. This cycle was repeated six times. Samples were then placed in a Sephadex G-200 column and spun at 2000× g for 5 minutes. Portions of the eluent were then used in PCR as described in Example 5, Experiment 6, run in gel electrophoresis and the bands visualized as described above (using the primers BR-SALa and BR-SALb).

Figure 9:
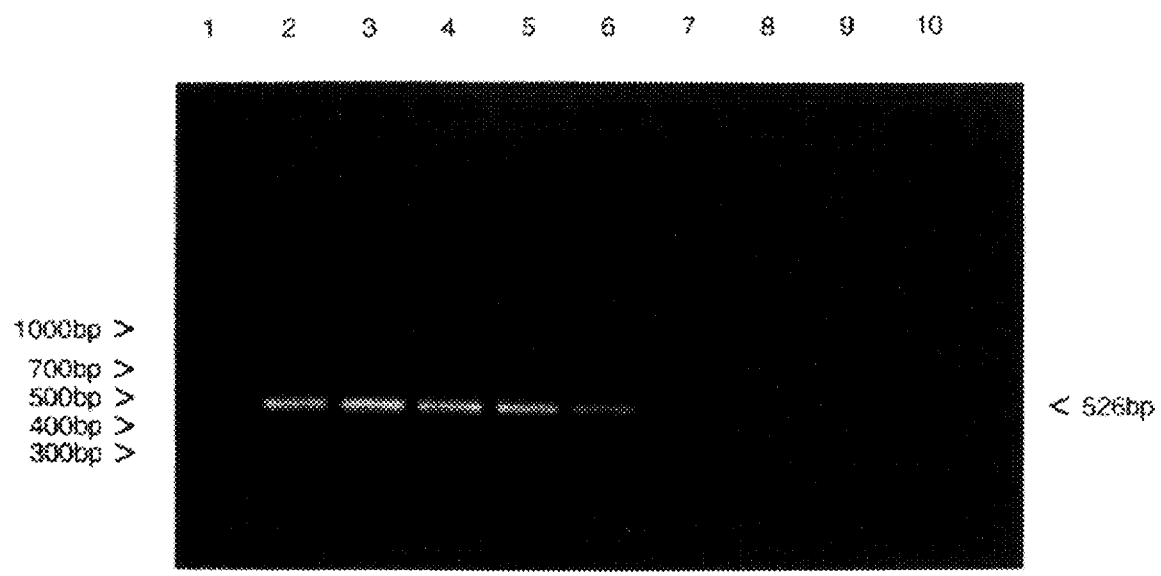
FIG. 9 is a gel showing detection of Salmonella in seeded sewage.

FIG. 9 shows the results obtained for these dilutions. Lane 1 contained marker DNA (BioVentures) (with bands corresponding to 1114, 900, 692, 501, 489, 404, 320, 240, 190, 147 and 124). Lane 2 was a control which contained sewage only, with no added organisms (i.e., an unseeded control). Lanes 3 through 9 contained dilutions $10^{-2}$, $10^{-3}$, $10^{-4}$, $10^{-5}$, $10^{-6}$, $10^{-7}$, $10^{-8}$ and $10^{-9}$ respectively. Lane 10 was a control containing 100 CFU, and no sewage. As shown in the figure, amplifiable DNA was present in the lower dilutions (lanes 3, 4 and 5). Southern blots were performed using standard methods (E. M. Southern, "Detection of specific sequences among DNA fragments separated by gel electrophoresis," J. Mol. Biol., 98: 503–517 (1975) and confirmed these results.

Primary treated sewage obtained from the Sand Island facility was also used in experiments designed to demonstrate direct detection of Salmonella in sewage.

EXAMPLE 7

PCR of Environmental Samples

Figure 10:
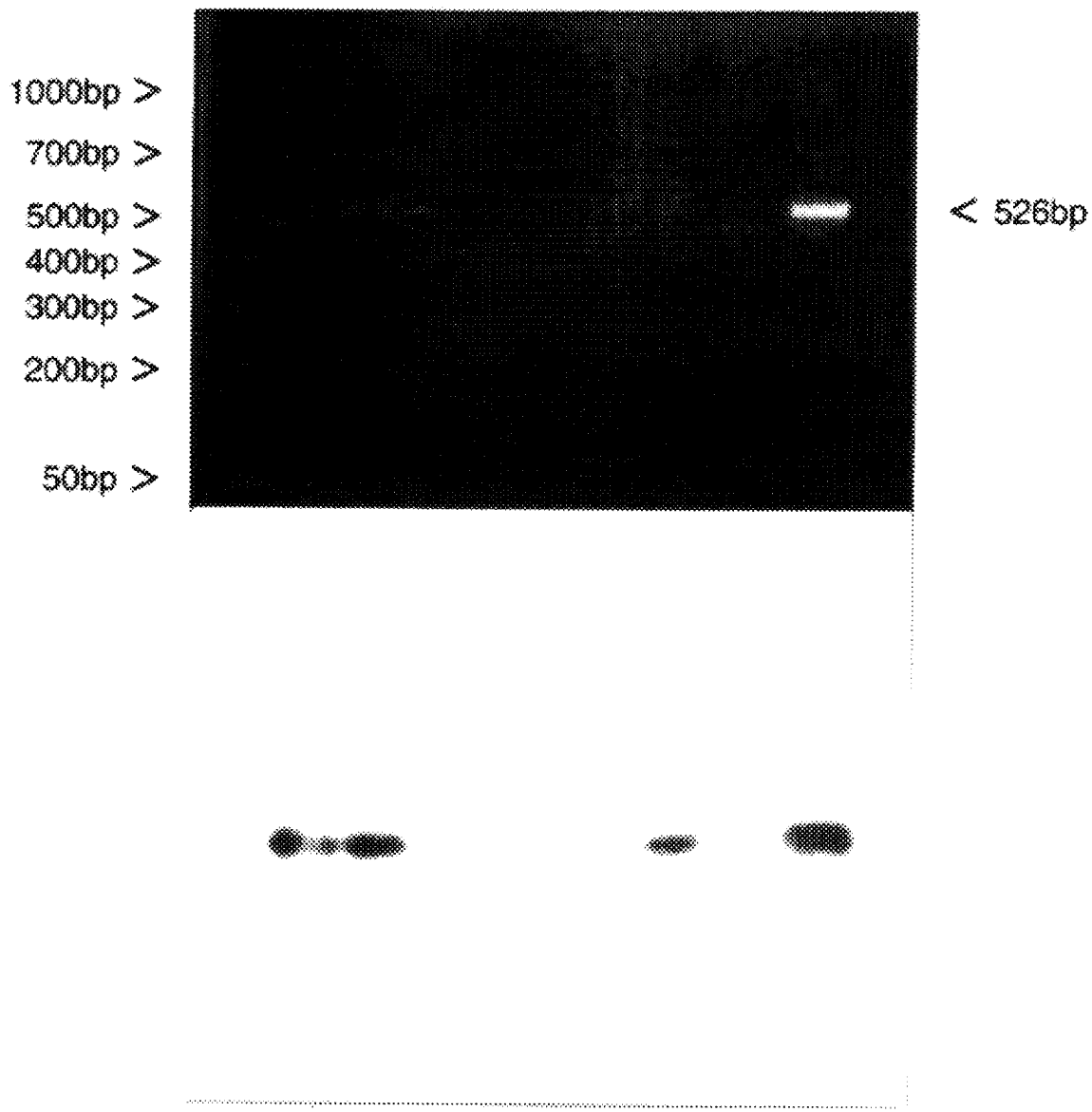
FIG. 10 is a gel showing detection of Salmonella in environmental water.

Samples obtained from environmental and sewage effluents processed as described above were tested using the optimal PCR conditions described in the above example and run on a gel. FIG. 10 shows the results obtained. Lane 1 contains marker DNA (BioVentures); Lane 2 contains is from Manoa Stream, Lanes 3 and 4 contain sewage effluent, Lane 5, 6 and 7 contain ocean water, Lane 8 is a negative control, and lane 9 is a positive control. As shown, the only positive band was observed with the positive control, indicating that no Salmonella was present in any of these environmental samples.

EXAMPLE 8

Nested Primer PCR Protocol for Salmonella

Figure 11:
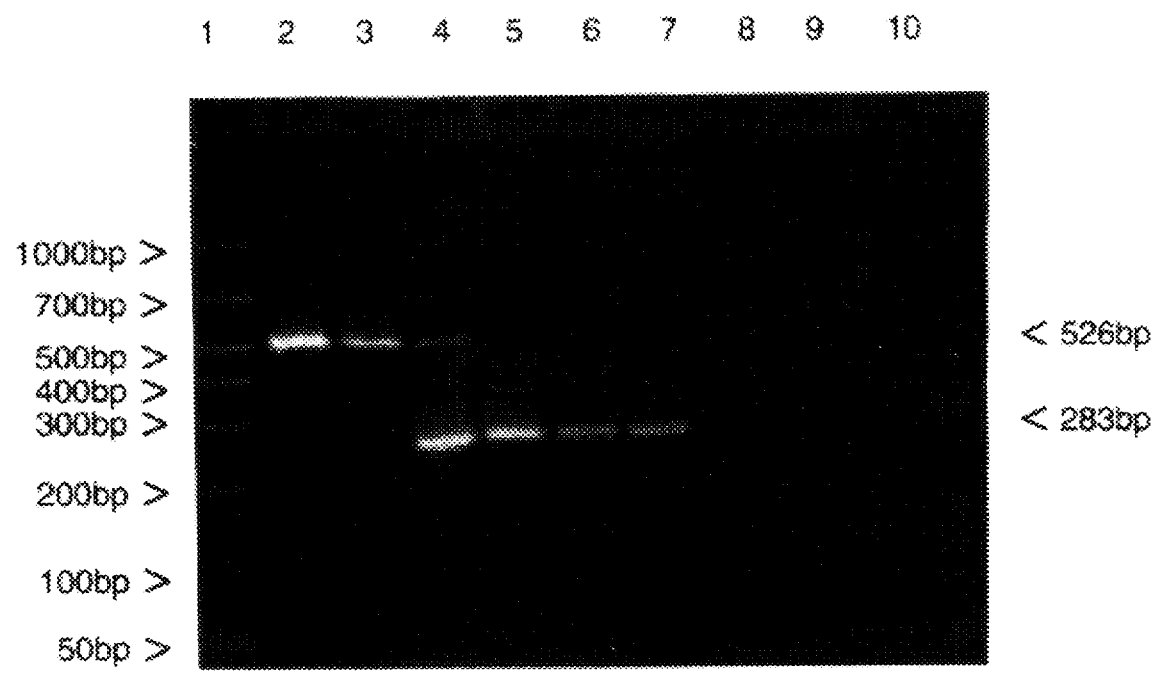
FIG. 11 is a gel showing PCR products obtained using nested PCR with Salmonella.

In addition to the PCR protocol using a single primer pair, a nested PCR protocol was developed. In this nested primer protocol, the first PCR step subjected to samples to 35 cycles, each consisting of 120 sec. at 94° C., 20 sec. at 57.5° C., and 60 sec. at 72° C., followed by 7 min. at 72° C. to complete synthesis. In the first PCR step primers BR-SAL and BR-SALa and BR-SALb were used. The second nested PCR step (using primers SAL-Ia & SAL-Ib) was carried out in a total volume of 100 µl, with a 2 µl sample of the first round of PCR used as the template. The cycle profile consisted of denaturation at 95° C. for 5 min followed by twenty cycles, each consisting of 30 sec. at 94° C., 60 sec. at 54° C., and 60 sec. at 72° C., followed by completion of synthesis at 72° C. for 10 min. The PCR products were analyzed by gel electrophoresis as described above. These results are shown in FIG. 11. In this Figure, Lane 1 contains marker; Lane 2 contains 200 pg; Lane 3 contains 20 pg; Lane 4 contains 2 pg; Lane 5 contains 200 fg; Lane 6 contains 20 fg; Lane 7 contains 2 fg; Lane 8 contains 200 ag; Lane 9 contains 20 ag; and Lane 10 contains control.

EXAMPLE 9

PCR of Shigella

Following the fine-tuning of the Salmonella PCR assay, a parallel assay was developed for rapid detection of Shigella species.

Multiple primers were developed, including primer ShigA (SEQ ID NO:6) and ShigB (SEQ ID NO:7), which were prepared from a previously published Shigella restriction fragment sequence (Hartman et al., "Sequence and molecular characterization of a multicopy invasion plasmid antigen gene, ipaH, of *Shigella flexneri*, J. Bacteriol., 172: 1905–1915 [1990]). These primers are shown in Table 6. The primers were produced with an automatic DNA synthesizer (ABI 381A; Applied Biosystems).

TABLE 6

Primers Used for Detection of Shigella

| Primer | Sequence | SEQ ID NO: |
|---|---|---|
| ShigA | 5'-TTG ACC GCC TTT CCG ATA C-3' | SEQ ID NO:6 |
| ShigB | 5'-ACT CCC GAC ACG CCA TAG A-3' | SEQ ID NO:7 |

These primers were designed such that they are compatible for use in combination with the Salmonella detection assays, while retaining the sensitivity and specificity of both assay systems.

As a control to determine whether these primers would produce cross-reactivity, all of the Shigella and non-enteric strains listed in Table 3 were tested using these primers and PCR testing protocols. The DNA extracts were prepared as described above in Example 2 for Salmonella, and the PCR cycle conditions were the same as those used in Experiment 6 of Example 3. The sequence shown in SEQ ID NO:8 was used as a probe to detect the presence of Shigella bands in gel electrophoresis. The same gel electrophoresis procedures as were used above for Salmonella were also used in this Example, with the exception that the Shigella probe was used. These data are not shown, but indicated that there was specific and sensitive amplification of Shigella DNA, without any problems associated with cross-reactivity.

Figure 12:
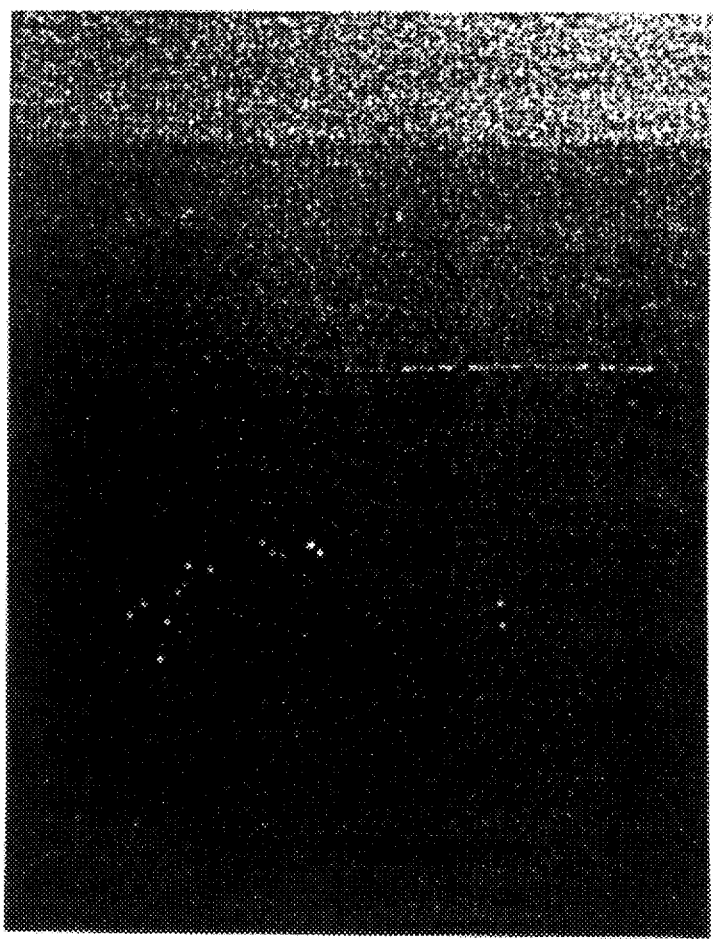
FIG. 12 is a gel showing PCR products obtained with Shigella.

FIG. 12, shows the results obtained for various dilutions S. dysenteriae DNA. In this figure, lane 1 was a molecular weight marker (Bio Ventures) (1000 bp, 700 bp, 525 bp, 500 bp, 400 bp, 300 bp, 200 bp, 100 bp, and 50 bp). Lane 2 contained 100 ng of S. dysenteriae genomic DNA; lane 3 contained 10 ng; lane 4 contained 1 ng; lane 5 contained 0.1 ng; lane 6 contained 100 pg; lane 7 contained 10 pg; lane 8 contained 1 pg; lane 9 contained 0.1 pg; lane 10 contained 100 fg; and lane 11 contained 10 fg.

As shown in this figure, good amplification was obtained with as little as 100 pg of S. dysenteriae DNA, and a detectable band was observed at 10 pg DNA.

EXAMPLE 10

Nested Primer PCR Protocol for Shigella

In addition to the PCR protocol using a single primer pair, a nested PCR protocol was developed. In this nested primer protocol, the first PCR step subjected to samples to 35 cycles, each consisting of 120 sec. at 94° C., 20 sec. at 57.5° C., and 60 sec. at 72° C., followed by 7 min. at 72° C. to complete synthesis. In the first PCR step, primers ShigA and ShigB were used. The second nested PCR step (using two additional primers, "Shig-Ia" and "Shig-Ib," as shown in the following Table), was carried out in a total volume of 100 µl, with a 2 µl sample of the first round of PCR used as the template. The cycle profile consisted of denaturation at 95° C. for 5 min followed by twenty cycles, each consisting of 30 sec. at 94° C., 60 sec. at 54° C., and 60 sec. at 72° C., followed by completion of synthesis at 72° C. for 10 min. The PCR products were analyzed by gel electrophoresis as described above (results not shown).

TABLE 7

Nested Primers Used for Detection of Shigella

| Primer | Sequence | SEQ ID NO: |
|---|---|---|
| Shig-Ia | 5'-ACG AGT CTT TCG CTG TT-3' | SEQ ID NO:8 |
| Shig-Ib | 5'-AAA CGC ATT TCC TTC AC-3' | SEQ ID NO:9 |

EXAMPLE 11

Figure 13:
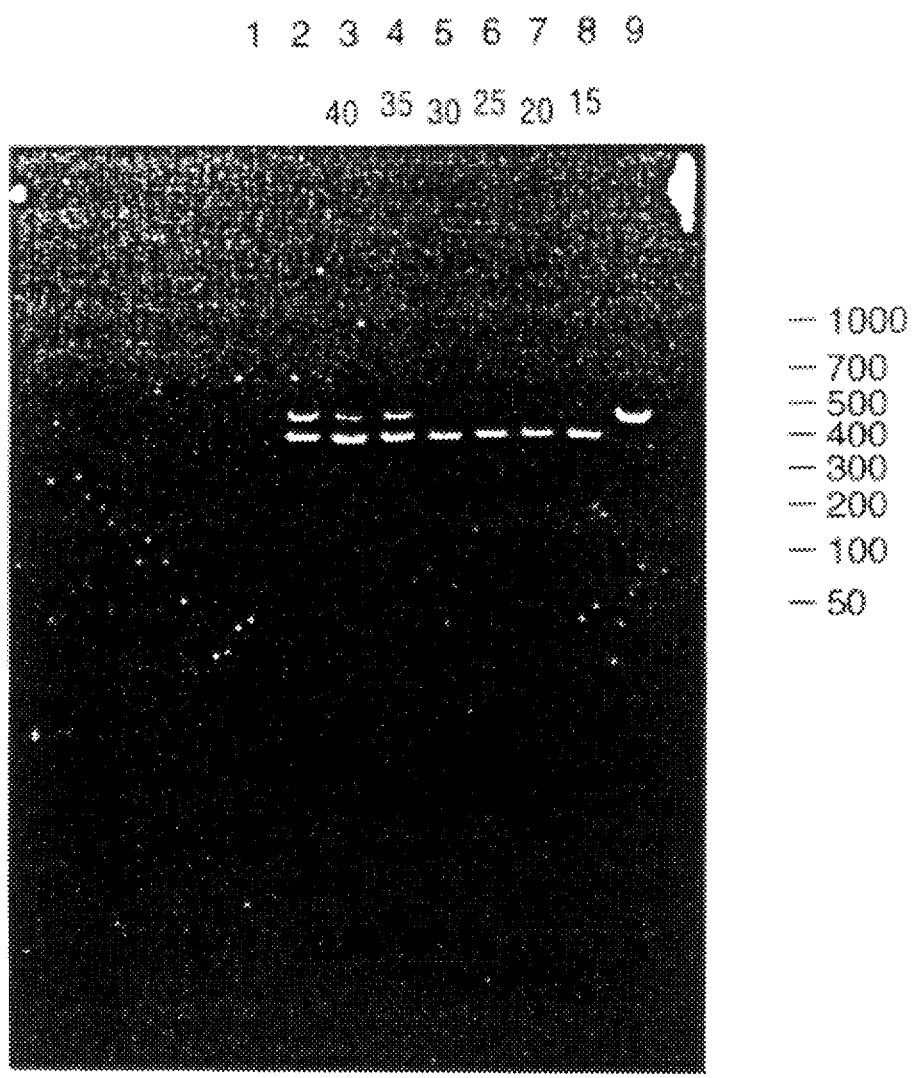
FIG. 13 is a gel showing PCR products obtained during simultaneous amplification of Salmonella and Shigella.

Multiplex PCR Amplification for Simultaneous and Specific Detection of Salmonella and Shigella In this experiment, specific DNA fragments from genomic DNAs of S. dysenteriae (ATCC #11456b) and S. typhimurium (ATCC #14028) were detected in a multiplex PCR system. The primers used in this experiment were the two Shigella primers (ShigA and ShigB) and the Salmonella primers designated BR-SALa and BR-SALb. The PCR reaction mix contained 100 ng of DNA from both organisms and 0.3 µM of each primer. The samples were run for 30 cycles of 94° C. for 2 min., 57.5° C. for 20 sec., and 72.0° C. for 1 min. As shown in FIG. 13, varying MgCl$_2$ concentrations were tested in this experiment. The reaction products were run on gels and visualized as described in the previous examples. In FIG. 13, Lane 1 contains molecular weight markers sized at 1000, 700, 525, 500, 400, 300, 200, 100, and 50 base pairs. Lane 2 shows simultaneous amplification of both Salmonella and Shigella with 40 mM MgCl$_2$. Lane 3 shows simultaneous amplification of both Salmonella and Shigella with 35 mM MgCl$_2$. Lane 4 shows simultaneous amplification of both Salmonella and Shigella with 30 mM MgCl$_2$. Lane 5 shows simultaneous amplification of both Salmonella and Shigella with 25 mM MgCl$_2$. Lane 6 shows simultaneous amplification of both Salmonella and Shigella with 20 mM MgCl$_2$. Lane 7 shows simultaneous amplification of both Salmonella and Shigella with 15 mM MgCl$_2$. Control lane 8 shows the 408 bp specific S. dysenteriae PCR product, and lane 9 shows the 525 bp specific S. typhimurium PCR product. The reaction mixture in these lanes was the usual composition, as described above.

Based on this experiment, it appears that good, specific amplification of S. dysenteriae and S. typhimurium were achieved at MgCl$_2$ concentrations ranging from 40–30 mM, with acceptable results observed with concentrations ranging from 25–20 mM. At 15 mM, the S. typhimurium fragment was virtually undetectable, although the S. dysenteriae fragment was readily apparent. Thus, conditions including 40 mM MgCl$_2$ appear optimal for the simultaneous amplification of S. typhimurium and S. dysenteriae DNA.

From the above, it is clear that the present invention provides the methods and compositions for the rapid, yet specific detection and identification of enteric organisms from various types of samples, including environmental and sewage samples. In addition, the present invention also provides the compositions and methods needed for the rapid definitive diagnosis of these pathogens. Indeed, the present invention clearly provides the compositions and methods needed for the rapid definitive diagnosis/detection/identification of two of the most important water-borne pathogens. Of particular importance is the fact that the present invention avoids problems associated with interfering substances often present in environmental samples, which may affect the amplification and/or detection of organisms.

It is not intended that the present invention be limited to a particular sample type. For example, it is contemplated that the present invention will be useful in various settings, including clinical, public health, and veterinary laboratories, as well as water quality, food and dairy laboratories.

---

What is claimed is:

1. A method for amplification of nucleic acid from one or more enteric pathogens comprising the steps of:

a) providing a test sample suspected of containing amplifiable nucleic acid from said one or more enteric pathogens;

b) isolating said amplifiable nucleic acid from said test sample;

c) combining said amplifiable nucleic acid with amplification reagents, and at least two primers selected from the group consisting of primers having the nucleic acid sequence set forth in SEQ ID NO:1, SEQ ID NO:2, SEQ ID NO:3, SEQ ID NO:4, SEQ ID NO:6 and SEQ ID NO:7, SEQ ID NO:8 and SEQ ID NO:9 to form a reaction mixture; and d) combining said reaction mixture with an amplification enzyme under conditions wherein said amplifiable nucleic acid is amplified to form amplification product.

2. The method of claim 1 further comprising the step of detecting said amplification product.

3. The method of claim 2, in which said detecting is accomplished by hybridization of said amplification product with a probe having the nucleic acid sequence set forth in SEQ ID NO:5.

4. The method of claim 2, in which said detecting is accomplished by hybridization of said amplification product with a probe selected from the group consisting of the nucleic acid sequences as set forth in SEQ ID NO:8 and SEQ ID NO:9.

5. The method of claim 1, wherein said primers hybridize to nucleic acid from said enteric pathogen selected from the group consisting of Salmonella and Shigella species.

6. The method of claim 1, wherein said test sample is selected from the group comprising sewage, sludge, soil, food, feed, and water.

7. A method for amplification of nucleic acid from a plurality of enteric pathogens comprising the steps of:

a) providing a test sample suspected of containing amplifiable nucleic acid of said plurality of enteric pathogens;

b) isolating said amplifiable nucleic acid from said test sample;

c) combining said amplifiable nucleic acid with amplification reagents, and all of the primers set forth in SEQ ID NO:1, SEQ ID NO:2, SEQ ID NO:6 and SEQ ID NO:7, to form a reaction mixture;

d) combining said reaction mixture with an amplification enzyme under conditions wherein said amplifiable nucleic acid is amplified to form amplification products; and e) detecting said amplification products.

8. The method of claim 7, wherein said detecting comprises hybridizing said amplification product with the probe having the nucleic acid sequences selected from the group consisting of SEQ ID NO:5, SEQ ID NO:8, and SEQ ID NO:9.

9. The method of claim 1, wherein said enteric pathogens consist of the Salmonella and Shigella species.

10. The method of claim 1, wherein said test sample is selected from the group comprising sewage, sludge, soil, food, feed, and water.

11. A method for amplification of nucleic acid from an enteric pathogen comprising the steps of:

a) providing a test sample suspected of containing amplifiable nucleic acid of said enteric pathogen;

b) isolating said amplifiable nucleic acid from said test sample;

c) combining said amplifiable nucleic acid with amplification reagents, and the primers set forth in SEQ ID NO:1 and SEQ ID NO:2, to form a first reaction mixture;

d) combining said reaction mixture with an amplification enzyme under conditions wherein said amplifiable nucleic acid is amplified to form a first amplification product;

e) combining said first reaction mixture with amplification reagents, and the primers set forth in SEQ ID NO:3, and SEQ ID NO:4, to form a second reaction mixture;

f) combining said second reaction mixture with an amplification enzyme under conditions wherein said amplifiable nucleic acid is amplified to form a second amplification product; and g) detecting said first or second amplification product.

12. The method of claim 11, wherein said detecting comprises hybridizing said amplification product with a probe having the nucleic acid sequence set forth in SEQ ID NO:5.

13. The method of claim 12, wherein said enteric pathogen is Salmonella.

14. The method of claim 12, wherein said test sample is selected from the group comprising sewage, sludge, soil, food, feed, and water.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ACGGTTGTTT AGCCTGATAC
                      20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTGGATGAGA TGGAAGAATG
                      20

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTTCGGCATT GTTATTTCT
                      19

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTCAGGGTCA TCGTTATTC
                      19

-continued ( 2 ) INFORMATION FOR SEQ ID NO:5:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

TACATCGTAA AGCACCATCG CAAAT    25

( 2 ) INFORMATION FOR SEQ ID NO:6:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

TTGACCGCCT TTCCGATAC    19

( 2 ) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

ACTCCGACA CGCCATAGA    19

( 2 ) INFORMATION FOR SEQ ID NO:8:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

AGCAGTCTTT CGCTGTT    17

( 2 ) INFORMATION FOR SEQ ID NO:9:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

AAACGCATTT CCTTCAC    17